(12) United States Patent
Davis et al.

(10) Patent No.: US 10,624,816 B2
(45) Date of Patent: Apr. 21, 2020

(54) ORAL ADMINISTRATION COUPLER

(71) Applicant: NEOMED, INC., Woodstock, GA (US)

(72) Inventors: Benjamin Martin Davis, Woodstock, GA (US); Aaron N. Ingram, Canton, GA (US); Mark M. Costello, County Mayo (IE)

(73) Assignee: NeoMed, Inc., Woodstock, GA (US)

( * ) Notice: Subject to any disclaimer, the term of this patent is extended or adjusted under 35 U.S.C. 154(b) by 351 days.

(21) Appl. No.: 15/078,674

(22) Filed: Mar. 23, 2016

(65) Prior Publication Data

US 2016/0279032 A1    Sep. 29, 2016

Related U.S. Application Data

(60) Provisional application No. 62/137,293, filed on Mar. 24, 2015, provisional application No. 62/192,726, filed on Jul. 15, 2015.

(51) Int. Cl.
| | |
|---|---|
| *A61J 15/00* | (2006.01) |
| *A61J 7/00* | (2006.01) |
| *A61M 5/142* | (2006.01) |
| *A61J 11/00* | (2006.01) |
| *A61M 5/31* | (2006.01) |

(52) U.S. Cl.
CPC ......... *A61J 7/0053* (2013.01); *A61J 11/0035* (2013.01); *A61J 15/0011* (2013.01); *A61M 5/142* (2013.01); *A61J 15/0076* (2015.05); *A61M 2005/3139* (2013.01); *A61M 2202/0482* (2013.01)

(58) Field of Classification Search
CPC .. A61J 7/0053; A61J 7/00; A61J 15/00; A61J 15/0011; A61J 13/00
See application file for complete search history.

(56) References Cited

U.S. PATENT DOCUMENTS

| | | | |
|---|---|---|---|
| 3,572,337 | A | 3/1971 | Schunk |
| 4,046,145 | A | 9/1977 | Choksi et al. |
| 5,244,122 | A | 9/1993 | Botts |
| 5,275,619 | A | 1/1994 | Engebretson et al. |
| 5,824,012 | A | 10/1998 | Burchett et al. |
| 5,891,165 | A | 4/1999 | Buckner |

(Continued)

FOREIGN PATENT DOCUMENTS

| | | |
|---|---|---|
| CA | 2548976 A1 | 12/2007 |
| EP | 1447072 A1 | 8/2004 |

(Continued)

OTHER PUBLICATIONS

Kasper et al.; "ENFit Enteral Connections: Are You Ready?"; Premier Safety Institute; Mar. 26, 2015; 5 pgs.

(Continued)

*Primary Examiner* — Deanna K Hall
(74) *Attorney, Agent, or Firm* — Dority & Manning, P.A.

(57) ABSTRACT

An improved oral administration coupler for delivery of fluids such as medications and nutritional fluids. Example oral administration couplers have a first end with an applicator for oral delivery to an infant, and a second end with a coupling compatible with an enteral fluid delivery syringe. A fluid delivery conduit extends in fluid communication from the first end to the second end, to deliver fluid from the syringe to the infant.

38 Claims, 18 Drawing Sheets

(56) References Cited

U.S. PATENT DOCUMENTS

| | | |
|---|---|---|
| 6,126,679 A | 10/2000 | Botts |
| 6,165,153 A | 12/2000 | Kashmer |
| 6,200,295 B1 | 3/2001 | Burchett et al. |
| 6,270,519 B1 | 8/2001 | Botts |
| 6,684,918 B1 | 2/2004 | Thilly et al. |
| 7,032,764 B2 | 4/2006 | Viggiano |
| 7,172,085 B2 | 2/2007 | Beaudette |
| 7,320,678 B2 | 1/2008 | Ruth et al. |
| 8,016,795 B2 | 9/2011 | Barrelle et al. |
| 8,070,721 B2 | 12/2011 | Kakish et al. |
| 8,568,365 B2 | 10/2013 | Reid |
| 8,882,725 B2 | 11/2014 | Davis |
| 8,945,182 B2 | 2/2015 | Oates, II et al. |
| 8,985,357 B1 * | 3/2015 | Strayer ............... A61J 11/0005 215/11.1 |
| 9,060,918 B1 | 6/2015 | Tomassini |
| 9,433,768 B2 | 9/2016 | Tekeste et al. |
| 9,656,022 B1 | 5/2017 | Russo |
| 9,814,870 B2 | 11/2017 | Jin et al. |
| 2005/0251096 A1 | 11/2005 | Armstrong et al. |
| 2008/0223807 A1 | 9/2008 | Botts |
| 2011/0218569 A1 | 9/2011 | Tesini et al. |
| 2012/0022457 A1 | 1/2012 | Silver |
| 2013/0098861 A1 | 4/2013 | Lair et al. |
| 2014/0051926 A1 * | 2/2014 | Oates, II ............... A61J 17/006 600/109 |
| 2014/0207063 A1 | 7/2014 | Hyun et al. |
| 2015/0164744 A1 | 6/2015 | Ingram et al. |
| 2015/0224031 A1 | 8/2015 | Methner |
| 2015/0231038 A1 | 8/2015 | Oates, II et al. |
| 2015/0238747 A1 | 8/2015 | Russo |
| 2016/0030293 A1 | 2/2016 | Dorsey et al. |
| 2016/0067422 A1 | 3/2016 | Davis et al. |
| 2016/0159635 A1 | 6/2016 | Davis et al. |
| 2016/0175201 A1 * | 6/2016 | Schuessler .......... A61J 15/0092 604/516 |
| 2016/0279032 A1 | 9/2016 | Davis et al. |

FOREIGN PATENT DOCUMENTS

| | | |
|---|---|---|
| EP | 2269685 A2 | 1/2011 |
| FR | 2930428 A1 | 10/2009 |
| WO | 9200717 A1 | 1/1992 |
| WO | 03072162 A2 | 9/2003 |
| WO | 2016154304 A1 | 9/2016 |
| WO | 2016205626 A1 | 12/2016 |
| WO | 2017011754 A1 | 1/2017 |

OTHER PUBLICATIONS

International Search Report & Written Opinion for PCT/US2017/042559; Dec. 7, 2017; 21 pgs.
Contentions of Medela LLC in letter [redacted] dated Sep. 18, 2017; 3 pgs.
International Search Report & Written Opinion for PCT/US2017/043747; Nov. 2, 2017; 14 pgs.
10 ml Liquid Medicine Dispenser / Oral Syringe with Filler Tube; 1 pg; date unknown.
Alternative Syringes Low Displacement Option PowerPoint Presention; Presented by Rork Swisher of Covidien; ISO 80369 Series Meeting; Berlin Germany; 11 pgs; Mar. 19, 2014.
Medi-Pals Oral Medication Dispenser; 1 pg; Jun. 19, 2012.
MediPop 3 in 1 Pacifier; 1 pg; date unknown.
New ISO Tubing Connector Standards: A Follow-Up to the Sentinel Event Alert Webinar PowerPoint Presention; www.jointcommission.org; 50 pgs; Dec. 3, 2014.
New Tube Feeding Connectors Webinar PowerPoint Presention; www.oley.org; 24 pgs; Jun. 24, 2014.
Oral Medication Dispenser; 1 pg; Jun. 19, 2012.
Oral Medication Nurser; 1 pg; Oct. 6, 2006.
Slap-Shot Flexible Oral Doser; 1 pg; date unknown.
International Search Report & Written Opinion for PCT/US2016/023771; 17 pgs; dated Jun. 27, 2016.
Guide to New Enteral Feeding Connections; Covidien; Dec. 31, 2015; 4 pgs.
Invitation to Pay Additional Fees for PCT/US2017/042559; Oct. 16, 2017; 15 pgs.

* cited by examiner

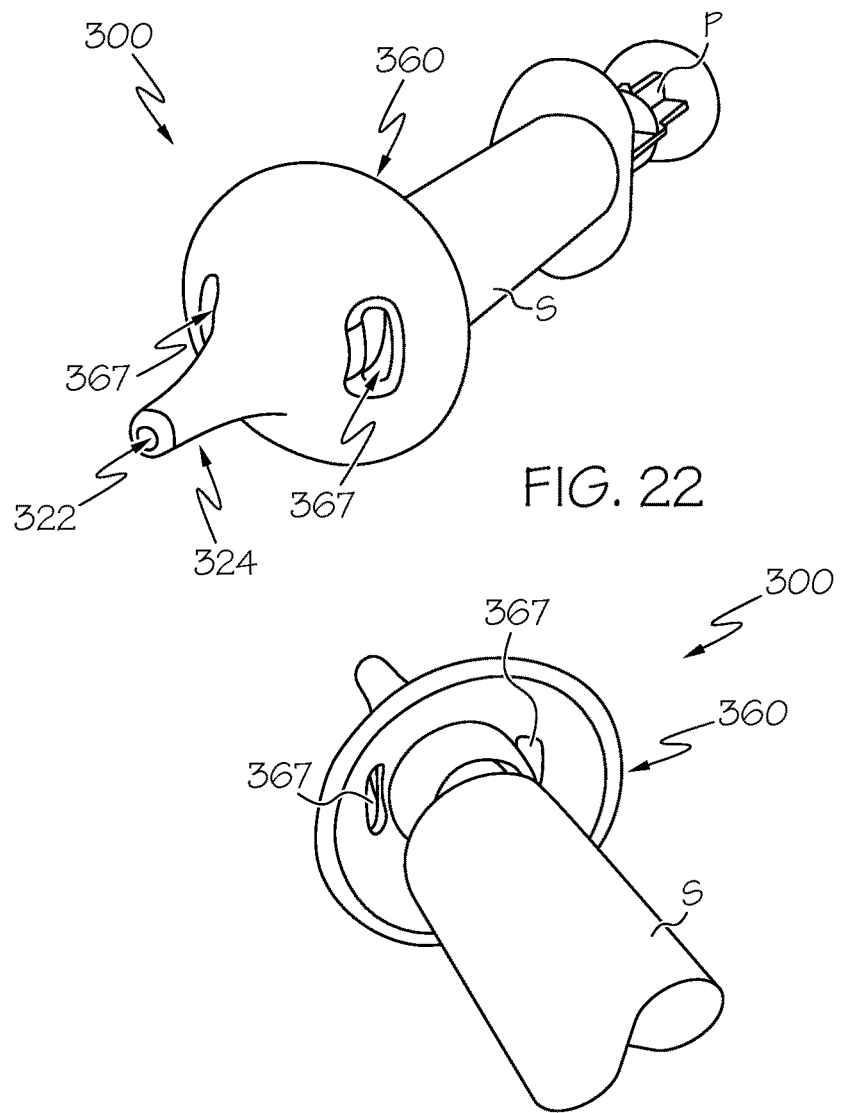
FIG. 22
FIG. 23
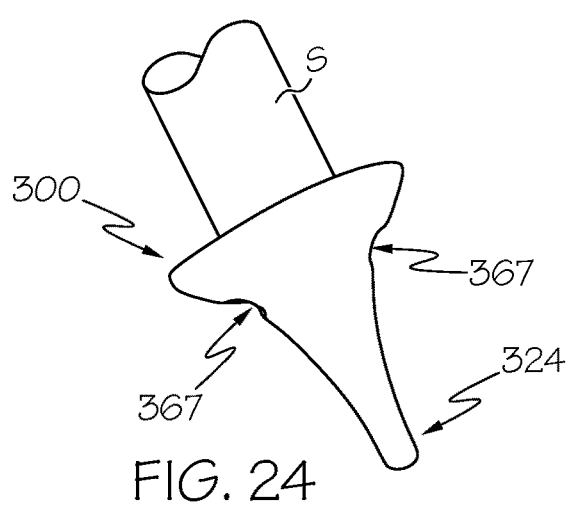
FIG. 24

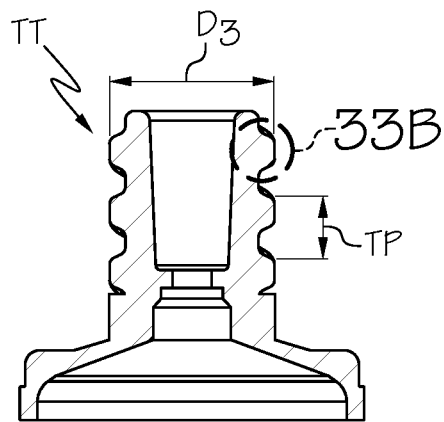 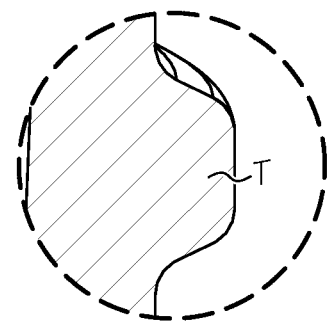
FIG. 33A        FIG. 33B
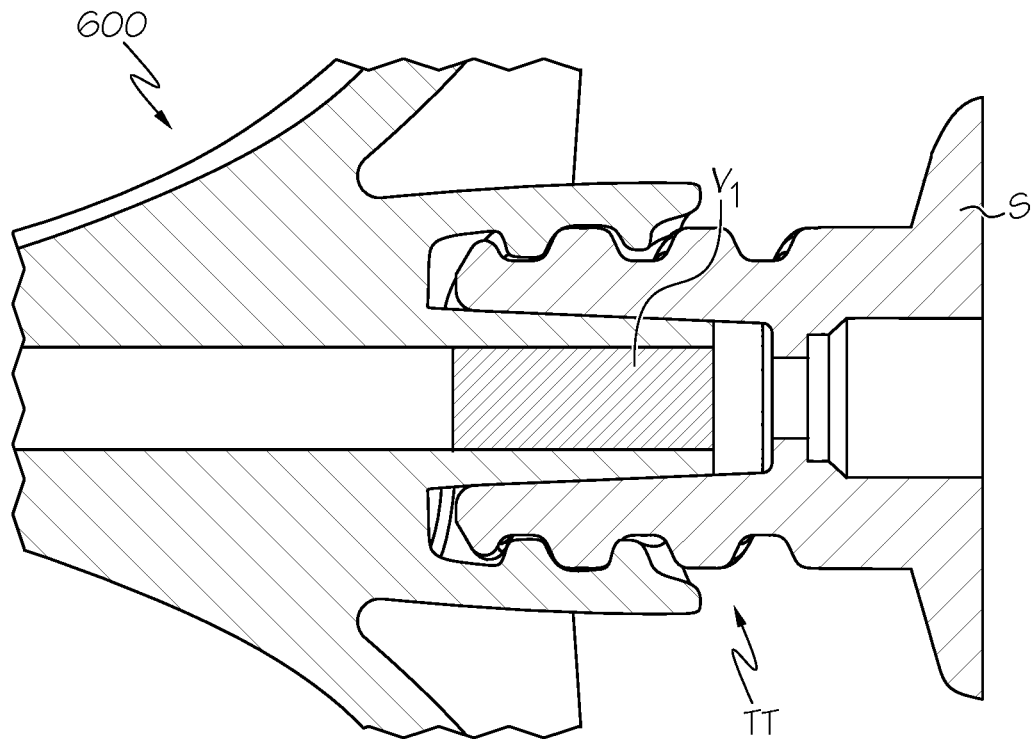
FIG. 34

ORAL ADMINISTRATION COUPLER

CROSS-REFERENCE TO RELATED APPLICATIONS

This application claims the priority benefit of U.S. Provisional Patent Application Ser. No. 62/137,293 filed Mar. 24, 2015 and U.S. Provisional Patent Application Ser. No. 62/192,726 filed Jul. 15, 2015, which are hereby incorporated herein by reference for all purposes.

TECHNICAL FIELD

The present invention relates generally to the field of containment, storage, and delivery of fluids, particularly in the medical and pharmaceutical fields, and more particularly to a coupler for devices used in oral administration of medical or nutritional fluids.

BACKGROUND

Various fluids such as medications and nutritional fluids are delivered to human or animal patients by dispensing from a syringe. Syringes conforming to the new ENFit enteral design standard (ISO 80369-3) may include nipple or tip couplings of larger dimension and volume or displacement than previous syringes. Volumetric differences in fluid delivery resulting from these changes may adversely affect accuracy of dosing in the oral administration of fluids.

Thus it can be seen that needs exist for improvements to oral administration couplers for fluid delivery and for providing a means to orally dose or dispense from the syringes conforming to the ENFit enteral design standard. It is to the provision of an improved oral administration coupler meeting these and other needs that the present invention is primarily directed.

SUMMARY

In example embodiments, the present invention provides an improved oral administration coupler for delivery of fluids such as medications and nutritional fluids. The invention further includes improved methods of design and manufacture of fluid delivery devices, including determining and controlling lumen size(s) and fluid flow path volume(s) so that the devices deliver accurate and consistent doses or quantities of fluid. Devices and methods according to the invention provide fluid volume paths or segments having the same or closely similar fluid delivery volume across a plurality of fluid delivery devices or accessories, for accurate and consistent dosing or fluid delivery quantities. For example, the fluid volume path of an oral administration coupler according to example forms of the invention has the same volume in the coupler as a male ENFit connector, at its nominal engagement depth.

In one aspect, the present invention relates to an oral administration coupler for delivering fluids from a syringe having a female connector to a cheek area of a child or infant. The oral administration coupler includes a conduit and a generally circumferential flange extending outwardly from the conduit. The conduit generally extends from a first end to a second end. The first end includes a generally elongate member for oral insertion to deliver fluids to the cheek area of the child or infant, and the second end includes an ENFit compatible fitting for removable engagement with the female connector of the syringe. The flange extending outwardly from the conduit is generally positioned between the first and second ends of the conduit.

In another aspect, the invention relates to an oral administration coupler including a central fluid transfer member, a lumen defined within the fluid transfer member, and a flange. The fluid transfer member generally includes a first end, a generally opposite second end, and an outer periphery. The lumen is defined within the central fluid transfer member and extends from the first end to the second end. The flange is generally positioned between the first and second ends of the fluid transfer member, and wherein the flange generally extends outwardly from an outer periphery of the central fluid transfer member.

In example embodiments, the first end of the central fluid transfer member includes a generally elongate stem having a substantially oval cross sectional shape. In one form, the generally elongate stem is generally duckbilled in shape. According to one form, the second end of the central fluid transfer member comprises an ENFit compatible coupling having a centrally-positioned transfer port and an outer collar comprising an internally threaded portion. Preferably, the ENFit compatible coupling is configured for removable engagement with a female connector of a syringe.

Optionally, the second end of the central fluid transfer member comprises a coupling having a centrally-positioned transfer port and an outer collar comprising an internally threaded portion. Preferably, the coupling is configured for removable engagement with a syringe having a threaded tip. In example forms, the threaded tip generally has an outer diameter and a thread pitch, the outer diameter being between about 4 to about 9 millimeters and the thread pitch being between about 1 millimeter to about 5 millimeters. In some example forms, the outer diameter is about 6.675 millimeters and the thread pitch is about 2.450 millimeters.

In still another aspect, the invention relates to an oral administration coupler for delivering fluids from a syringe to a cheek area of a child or infant. In example forms, the syringe has a threaded tip having an outer diameter of between about 4 millimeters to about 9 millimeters and a thread pitch of between about 1 millimeter to about 5 millimeters. The oral administration coupler generally includes a conduit and a flange. The conduit generally extending from a first end to a second end, wherein the first end includes a generally elongate oral delivery applicator for oral insertion to deliver fluids to the cheek area of the child or infant, and wherein the second end includes a coupling for removable engagement with the threaded tip of the syringe. The flange generally extends outwardly from the conduit and is generally positioned between the first and second ends of the conduit.

In yet another aspect, the invention relates to a method of designing a fluid delivery device including calculating a volume of at least a portion of a fluid delivery path of a first fluid delivery device; and designing a fluid delivery path of a second fluid delivery device to substantially match the fluid delivery path volume of the first fluid delivery device. In example forms, the first fluid delivery device includes a pharmacy coupler for transferring fluids from a container to a syringe. According to one example form, the second fluid delivery device includes an oral administration coupler for delivering fluids from a syringe to a cheek area of a child or infant.

BRIEF DESCRIPTION OF THE DRAWINGS

FIG. 22 shows a front perspective view of an oral administration coupler according to another example embodiment of the present invention, and showing the coupler removably mounted to a syringe and having one or more openings provided in a flange thereof.

FIG. 23 shows a rear perspective view of the oral administration coupler and syringe of FIG. 22.

FIG. 24 shows a top perspective view of the oral administration coupler and syringe of FIG. 22.

FIG. 33A is a cross-sectional view of a portion of one of the syringes taken along line 33A-33A of FIG. 32.

FIG. 33B is a detailed view of a thread portion of the syringe portion of FIG. 31A.

FIG. 34 is a cross-sectional view of the oral administration coupler removably engaged with the syringe as shown in FIG. 31.

DETAILED DESCRIPTION OF EXAMPLE EMBODIMENT

Figure 1:
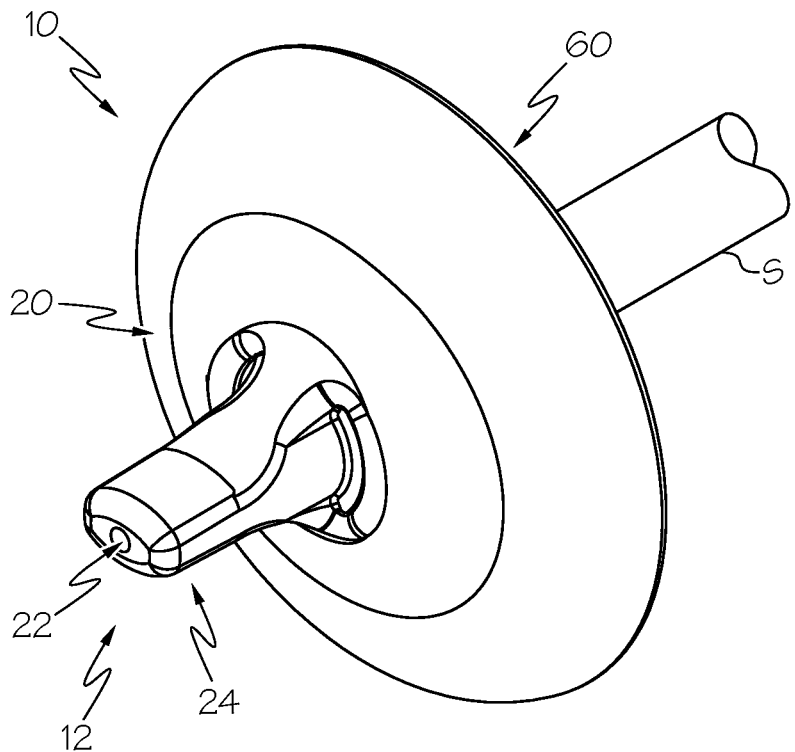
FIG. 1 shows a front perspective view of an oral administration coupler according to an example embodiment of the present invention, and further shows a syringe removably coupled thereto for dispensing contents from the syringe and through the oral administration coupler.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, the present invention relates generally to an oral administration coupling for attachment to a connector of a syringe. In some example forms, the connector of the syringe comprises an ENFit connector, for example, a female connector FC in the form of an ENFit female connector according to the global design standard ISO 80369-3. In other example embodiments, the connector of the syringe comprises a threaded tip.

Figure 2:
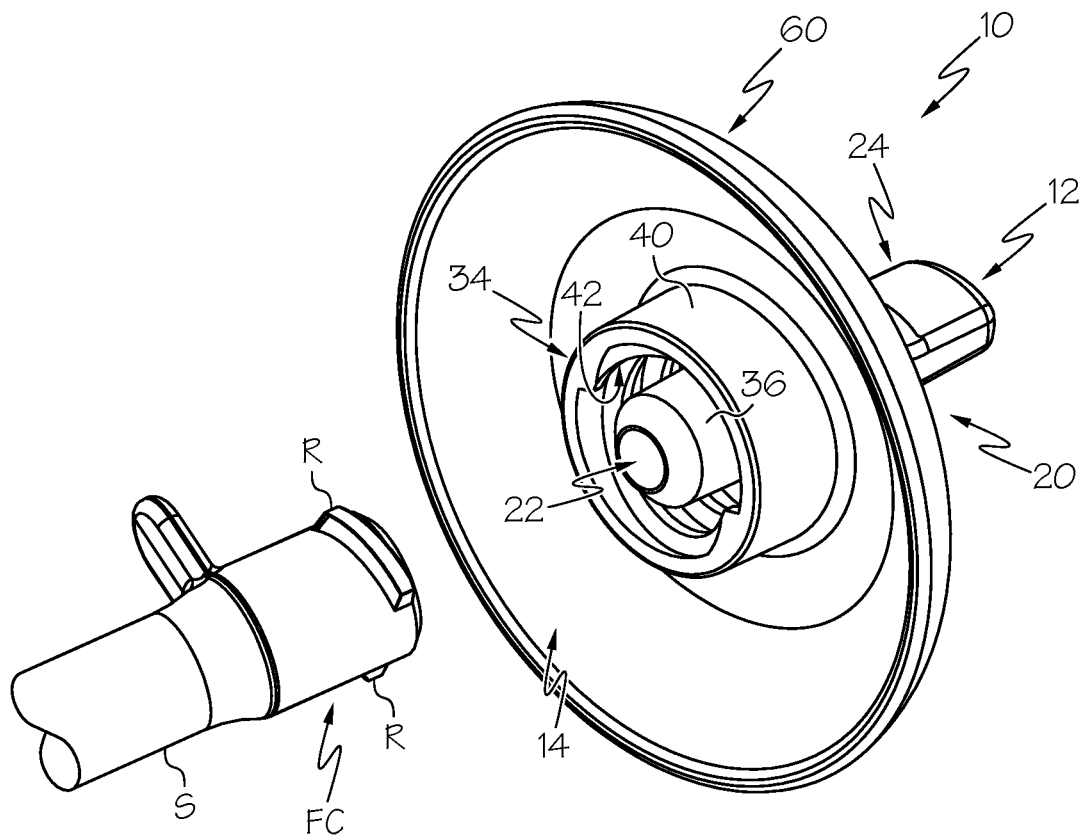
FIG. 2 shows a rear perspective view of the oral administration coupler of FIG. 1, and showing the syringe removably disengaged therefrom.

With respect to the ENFit connector, the female connector FC comprises a pair of thread lugs or ribs R extending along a portion of the periphery of the connector (see FIG. 2). Preferably, the oral administration coupling (as several embodiments will be described below) provides for removable engagement with the female connector FC. Typically, as will be described below, the coupling comprises a collar having a threaded internal portion for removable engagement with the ribs R of the female connector FC. Optionally, in other example embodiments, the coupling can be in the form of a non-threaded, slip-fit connection.

FIGS. 1-7 show an oral administration coupler 10 according to an example embodiment of the present invention. As depicted, the oral administration coupler 10 generally comprises a central fluid transfer member 20 extending from a first end 12 to a second end 14, and an outer flange 60 generally positioned between the first and second ends 12, 14 of the central fluid transfer member 20 and extending outwardly therefrom.

Figure 7:
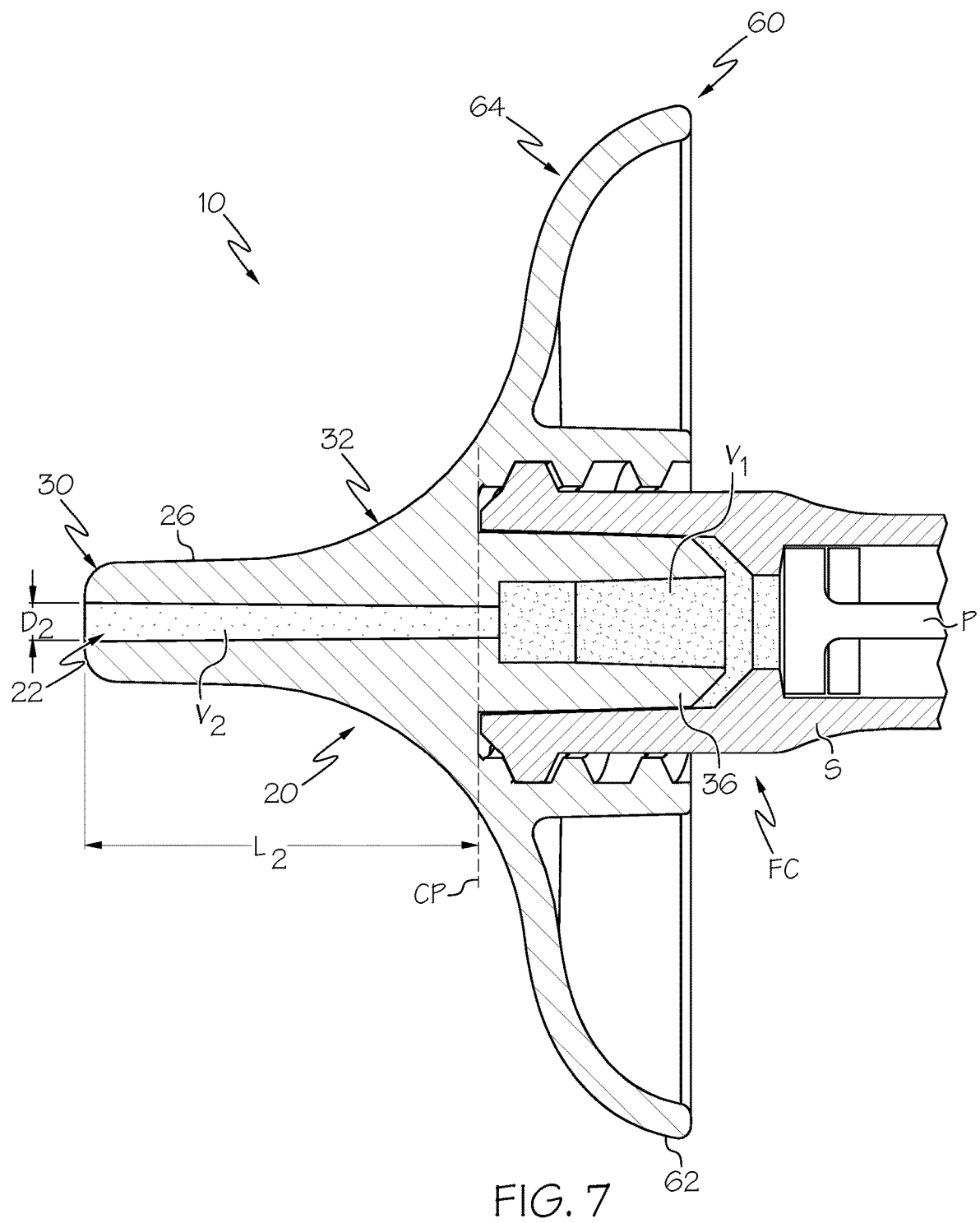
FIG. 7 shows a cross-sectional view of the oral administration coupler removably coupled with the syringe of FIG. 1.

The central fluid transfer member 20 generally comprises an elongate stem or oral delivery applicator 24 at the first end 12 of the fluid transfer member 20 and an ENFit compatible coupling or connector 34 positioned at the second end 14 of the fluid transfer member 20. In example forms, the oral delivery applicator 24 generally extends in a direction that is substantially opposite to the direction of the extension of the connector 34. The flange 60 is generally integrally formed with the fluid transfer member 20 between the first and second ends 12, 14 of the fluid transfer member 20. As shown in FIGS. 2 and 7, the female connector FC of the syringe S is preferably configured for removable coupling and sealing engagement with the coupling 34, for example, so that fluids within the syringe S can be transferred through the coupling 10 and orally administered to a human or animal patient by actuation of a plunger P movably mounted within the syringe S. Preferably, a lumen 22 is provided within the fluid transfer member 20 and extends between the first and second ends 12, 14, for example, through the entirety of both the oral delivery applicator 24 and the ENFit compatible coupling 34, providing fluid communication from the inlet end 14 of the coupler 10 at the syringe S, to the outlet end 12 of the coupler at the delivery applicator 24.

Figure 3:
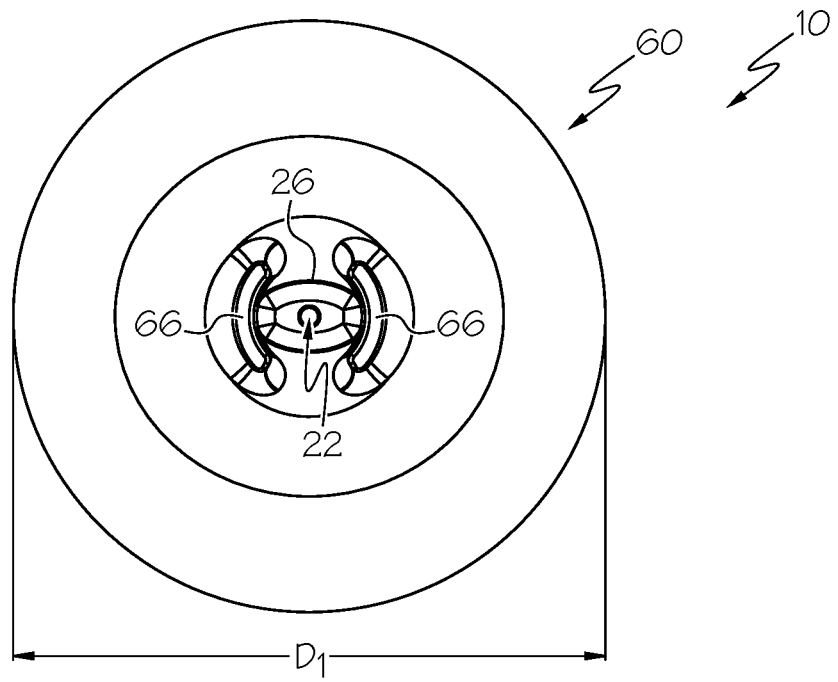
FIGS. 3-6 show several views of the oral administration coupler of FIG. 1.
Figure 4:
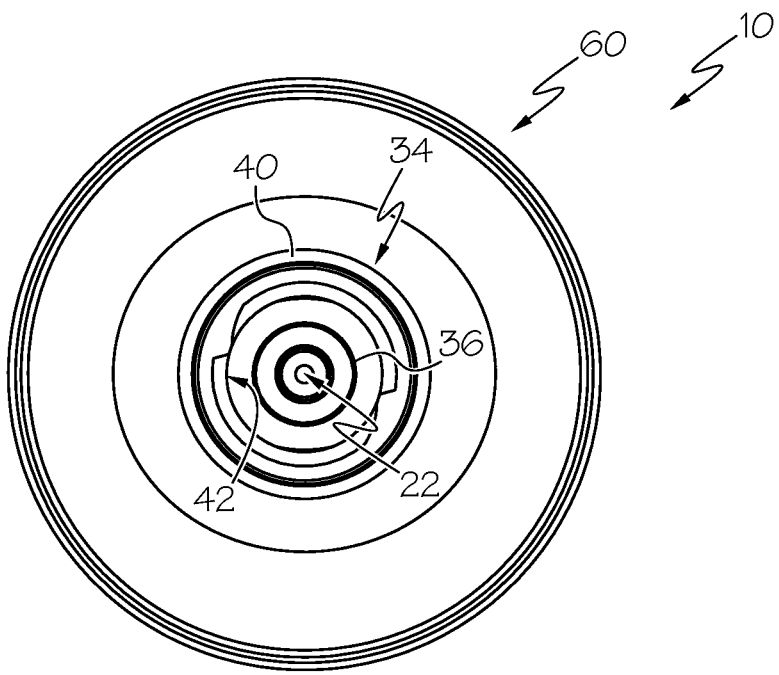
Figure 5:
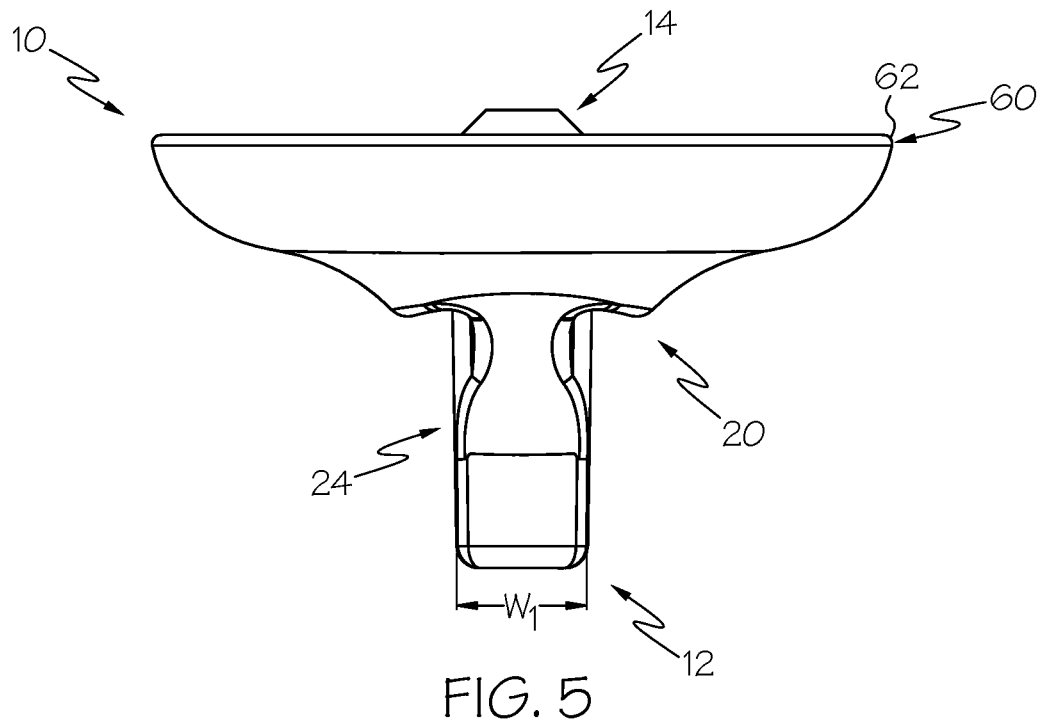

In example embodiments, the oral delivery applicator 24 is generally in the form of an irregular or asymmetric nipple, which is generally duckbilled in shape and has a generally non-circular or oval cross-section (see FIG. 3). For example, in example forms, the applicator 24 generally comprises a width $W_1$ that is generally greater than its height or thickness $T_1$ (see FIGS. 5-6). In some example forms, the width $W_1$ is generally between about 3.5 millimeters to about 6.5 millimeters, more preferably about 5.814 millimeters, and the thickness $T_1$ is generally between about 2 millimeters to about 5 millimeters, more preferably about 3.814 millimeters. Optionally, the applicator 24 can be shaped as desired, for example, extending generally linearly, curved, arcuate, hooked or otherwise extending as desired, having the shape of a rounded cylinder or flattened cylinder, and can be symmetric or asymmetric. Furthermore, the cross-sectional shape can be generally oval, ellipse, generally circular, or otherwise shaped as desired. According to some example forms, the applicator 24 comprises a substantially smooth outer periphery 26 having a generally radiused end 30 defined at the first end 12 of the fluid transfer member 20 and a generally radiused transition 32 defined between the applicator 24 and the flange 60 (see FIG. 6).

Referring back to FIG. 2, the ENFit compatible coupling 34 generally comprises a central transfer port 36 that is generally centrally positioned within an outer collar member 40. In example forms, the outer collar member 40 comprises an internally threaded portion 42 for providing removable engagement with the ribs R of the female coupling FC (see FIGS. 2 and 7). The lumen 22 is generally axially positioned with the transfer port 36, which extends from the second end 14 near the port 36 to the first end 12 near the end of the oral delivery applicator 24. Optionally, in some example forms, the coupling 34 only comprises the central transfer port, for example, such that the coupling 34 is in the form of a non-threaded, slip-fit connector. In example forms, the coupling 34 of the oral administration coupler 10 forms a fluid-tight, leak-proof seal with the female coupling FC of the syringe S, for fluid delivery from the syringe through the oral administration coupler.

In example embodiments, the oral administration coupler 10 is preferably sized and shaped to provide for oral insertion and dispensing of fluids near the cheek area of a child or infant. Furthermore, the flange 60 of the oral administration coupler 10 is generally sized to be substantially large for preventing a child or infant from choking on the coupling. According to one example form, the oral delivery applicator 24 defines a length $L_1$ extending between the first and second ends 12, 14 thereof, and the flange 60 defines an outer periphery 62 defining a diameter $D_1$ (see FIGS. 3 and 6). According to example forms, the length $L_1$ is generally between about 15 to about 35 millimeters, more preferably about 25 millimeters, and about 20.350 millimeters according to one example embodiment. The diameter $D_1$ of the flange 60 is generally between about 20 millimeters to about 40 millimeters, more preferably about 30 millimeters, and about 32.835 millimeters according to one example embodiment. Optionally, according to additional example embodiments of the present invention, the length $L_1$ and the diameter $D_1$ can be chosen as desired.

Figure 6:
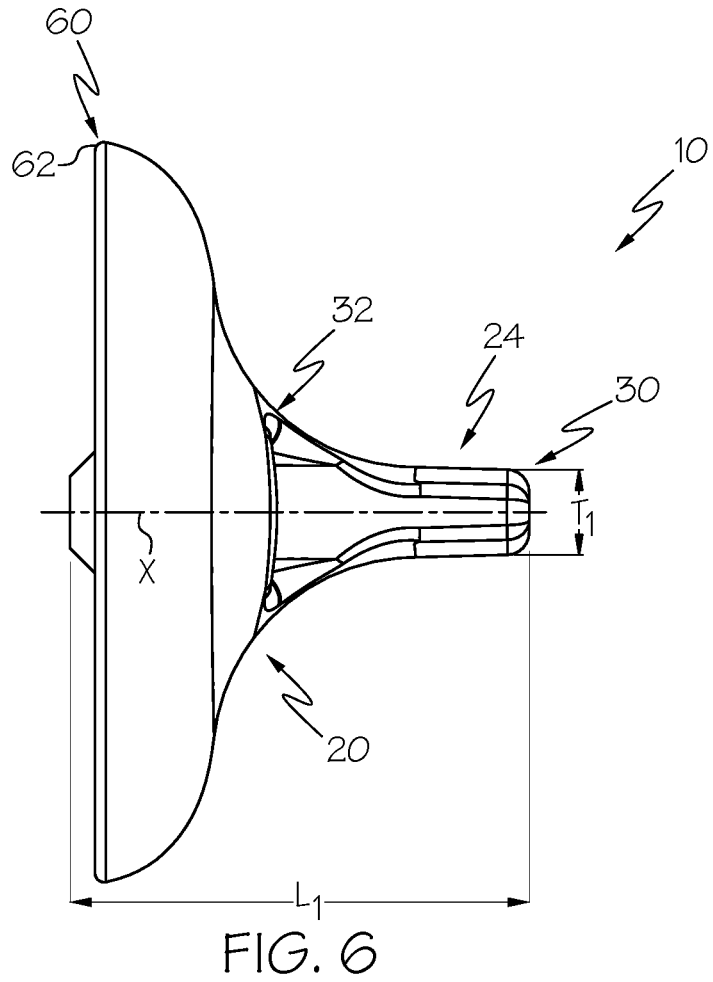

As depicted in FIG. 6, the central transfer port 36 generally extends beyond the flange 60. However, according to other example embodiments of the present invention, the central transfer port 36 can be shortened (or the flange 60 can be extended) such that the central transfer port 36 is generally recessed within the flange 60.

In the depicted embodiment, the flange 60 is generally circular in shape and projects generally outwardly and radially from the central fluid transfer member 20, for example, so as to form a generally circular skirt-like flange extending from the fluid transfer member 20. As described above and shown in FIG. 7, the flange 60 comprises the radiused transition 32 formed with the oral delivery applicator 24, and an outer portion of the flange 60 generally comprises a radiused surface profile 64 that extends to the outer periphery 62. Preferably, the transitions, contours or other geometrical shapes of the flange 60 can be chosen as desired. In some example forms, the flange 60 generally comprises an undulating profile having one or more peaks and valleys, or a portion of one or both. Preferably, the flange 60 substantially shields the connection of the coupler 10 with the syringe S, for example, so as to substantially prevent the connection from being exposed to the human or animal patient receiving the fluids from the syringe. Preferably, the radiused surface profile (including the radiused transition 32) provides for a comfortable contact surface with the patient, for example, when the applicator 24 is inserted to deliver the fluids.

In some example forms, one or more insets, indents or recesses 66 can be formed with the flange 60. For example, as shown in FIGS. 1, 3, 5 and 6, the a pair of generally radially-shaped recesses 66 are formed within a portion of the flange 60 generally near the radiused transition 32, for example, generally positioned between the oral delivery applicator 24 and the flange 60. In some forms, the recesses 66 act as mold reliefs such that the oral administration coupler 10 can be appropriately molded, for example, by plastic injection molding. Alternatively the recesses 66 can serve as vents or suction relief ports.

In example forms, the ENFit female coupling FC is substantially large (size and volume-wise) relative to known couplings, and thus, when withdrawing and dispensing a liquid medication or nutrients to/from the syringe, it is highly probable that a substantially large discrepancy lies between the amount of liquid filled into the syringe relative to the amount of liquid dispensed therefrom, thereby altering the accuracy of the dosage. In some forms, for example when dealing with small doses, a small volume difference may result in 15% or more in the dose difference.

In some example forms, a pharmacy coupler is used to fill the syringe, which has a male tip that displaces the volume of the syringe tip. Preferably, the volume of the oral administration coupling generally matches the volume displaced by the pharmacy coupler, thereby ensuring that the volume of the dose delivered from the oral administration coupling is the volume of the dose filled within the syringe. Thus, according to one form, the lumen size is controlled such that the administered dose is accurate. In example forms, the invention optionally includes a multi-component enteral fluid dispensing and delivery system, for example comprising any two or more of a pharmacy coupler, a syringe, a closure cap, and/or an oral administration coupler, for example according to any of the forms disclosed herein.

In preferred forms, the fluid volume path is substantially the same volume in the female coupling FC as the male ENFit connector or male coupling portion extending from within a portion of the presently claimed coupling. For example, as depicted in FIG. 7, a volume $V_1$ is defined within the female coupling FC and within a portion of the lumen 22 of the coupling, which is generally about 60 mm³. Optionally, the volume defined therein can be between about 40 mm³ to about 70 mm³, more preferably about 50 mm³. As such, a volume $V_2$ is defined within the lumen 22 generally extending through the delivery applicator 24, which comprises a length $L_2$ and a diameter $D_2$. Preferably, the volume $V_1$ is substantially similar to the volume $V_2$, for example, which is generally between about ±1 mm³. For example, the length $L_2$ is defined between the first end 12 and the end of the female connector FC or a cut-off plane CP. In some example forms, the lumen 22 adjacent the applicator 24 comprises a substantially uniform diameter $D_2$, which defines the volume $V_2$. Optionally, the lumen can comprise some taper or draft such that the diameter of the lumen 22 varies along the length $L_2$.

According to example forms, the length $L_2$ of the lumen 22 within the applicator 24 can be chosen as desired, for example, which will affect the diameter $D_2$ (and length $L_1$) to ensure the volume $V_2$ is substantially similar to the volume $V_1$. According to example forms, the length $L_2$ can generally be between about 20 millimeters to about 50 millimeters and generally comprise the volume $V_2$ of about 60 mm³. For example, according to example forms, when the length $L_2$ is about 20 millimeters, the diameter $D_2$ is about 1.95 millimeters and the volume $V_2$ is about 59.7 mm³; when the length $L_2$ is about 25 millimeters, the diameter $D_2$ is about 1.75 millimeters and the volume $V_2$ is about 60.13 mm³; when the length $L_2$ is about 30 millimeters, the diameter $D_2$ is about 1.60 millimeters and the volume $V_2$ is about 60.32 mm³; when the length $L_2$ is about 35 millimeters, the diameter $D_2$ is about 1.47 millimeters and the volume $V_2$ is about 59.4 mm³; when the length $L_2$ is about 40 millimeters, the diameter $D_2$ is about 1.38 millimeters and the volume $V_2$ is about 59.83 mm³; and when the length $L_2$ is about 50 millimeters, the diameter $D_2$ is about 1.25 millimeters and the volume $V_2$ is about 61.4 mm³. Optionally, other lengths and diameters can be chosen as desired, for example, to ensure the volume $V_2$ is substantially similar to the volume $V_1$.

Figure 8:
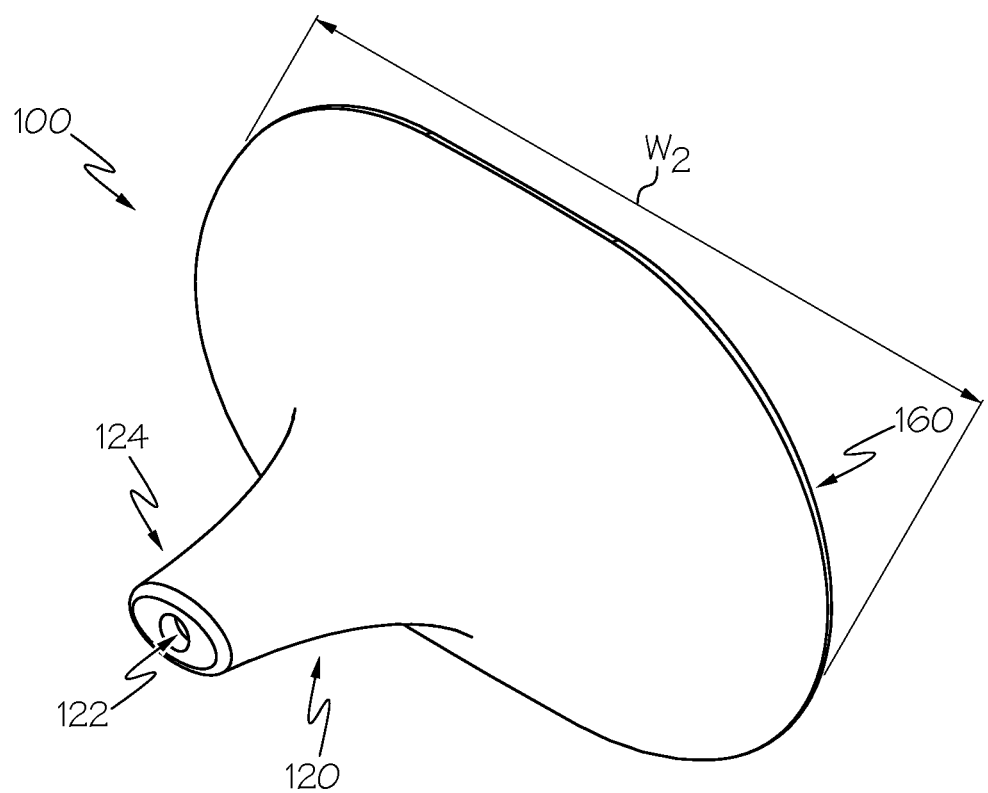
FIG. 8 shows a front perspective view of an oral administration coupler according to another example embodiment of the present invention.
Figure 9:
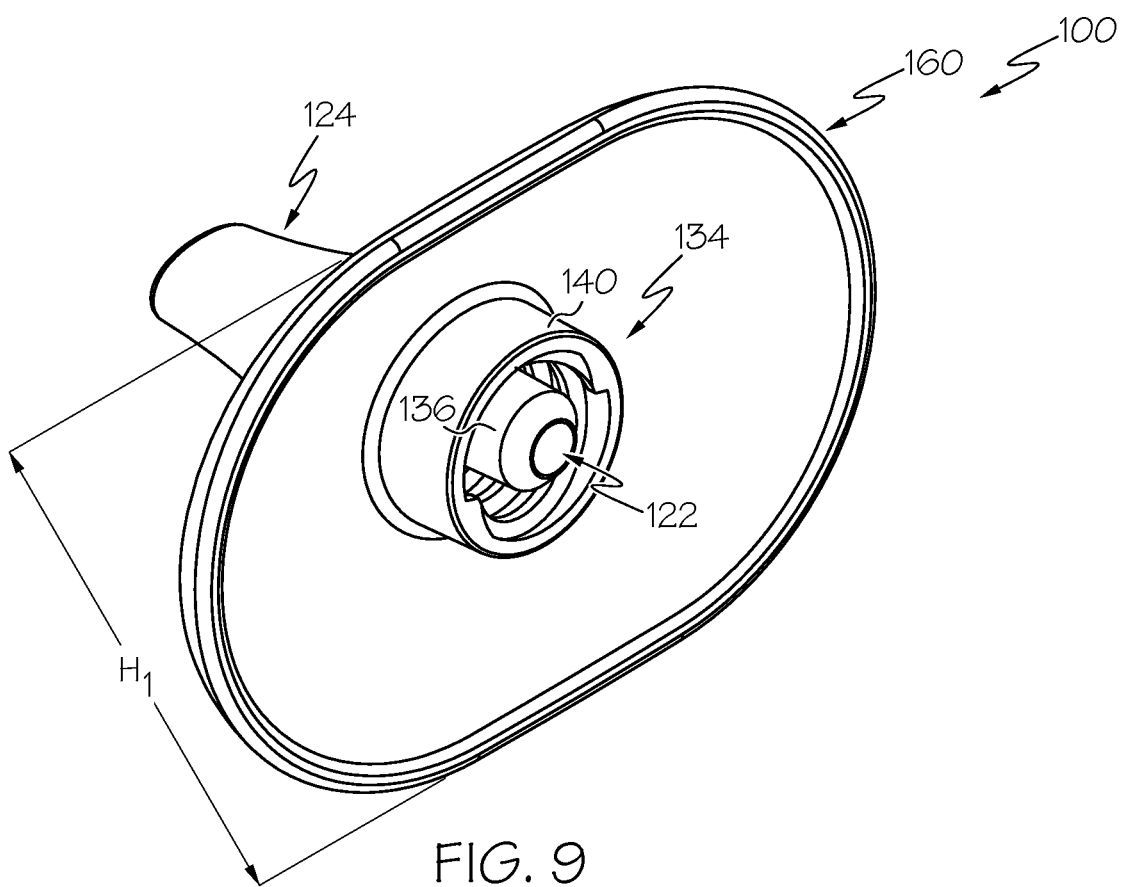
FIG. 9 shows a rear perspective view of the oral administration coupler of FIG. 8.

FIGS. 8-9 show an oral administration coupler 100 according to another example embodiment of the present invention. As depicted, the coupler 100 comprises a central fluid transfer member 120 having an oral administration applicator 124 and an ENFit compatible coupling 134, and whereby a lumen 122 is generally defined therein and extends between the ends thereof. A flange 160 generally extends outwardly from the central fluid transfer member and generally between the oral administration applicator 124 and the coupling 134. In example embodiments, the outer periphery 162 of the flange 160 is generally non-circular, for example, having two generally opposing radiused ends defining a width W2 and a height H1. In example forms, the width W2 is at least partially larger than the height H1. In example forms, the oral administration applicator 124 is generally similar to the applicator 24 as described above.

Figure 10:
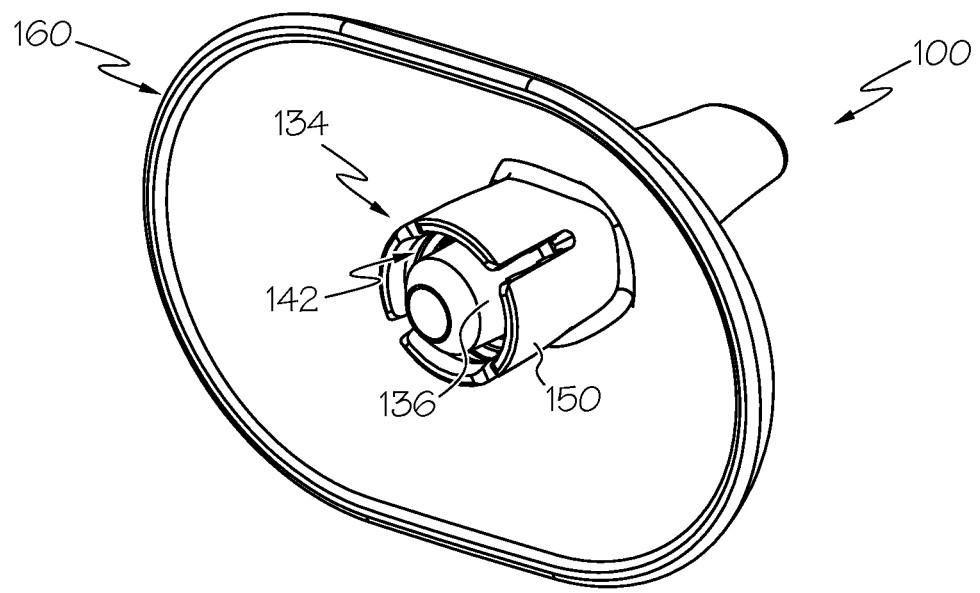
FIG. 10 shows a rear perspective view of an oral administration coupler according to another example embodiment of the present invention.
Figure 11:
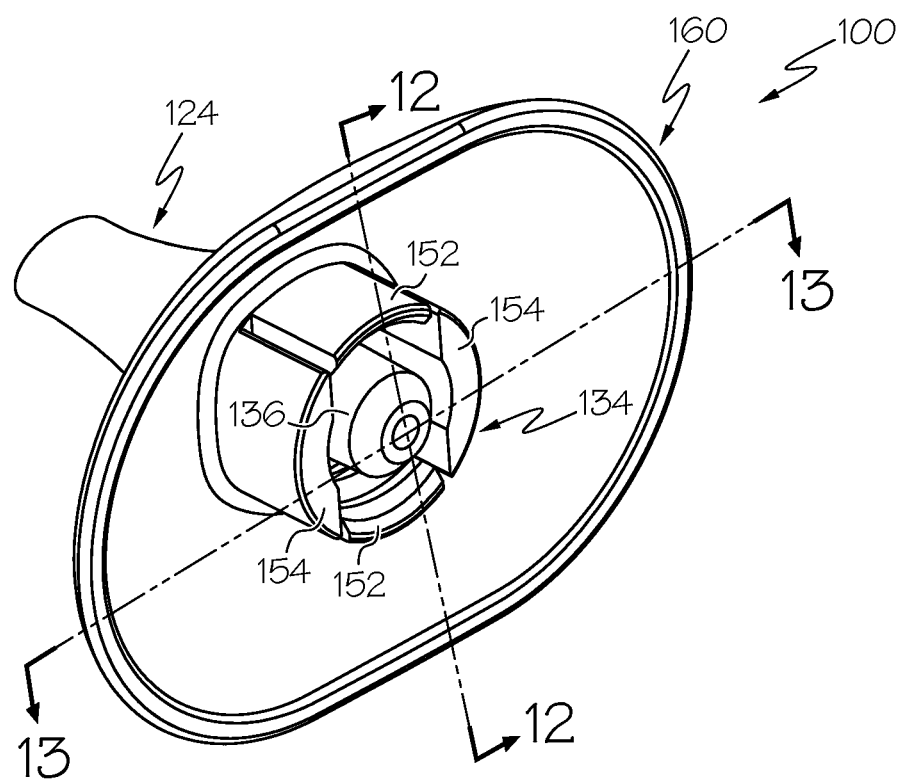
FIG. 11 shows a rear perspective view of an oral administration coupler according to another example embodiment of the present invention.

According to example form, the collar 140 of ENFit compatible coupling 134 can be configured to have one or more resilient and partially flexible clips or fingers 150, for example about four fingers 150 generally spaced radially around the port 136, for providing a push-on or snap-fit coupling engagement with the female connector FC of the syringe S (see FIG. 10). Thus, optionally, instead of screwing or rotating one of the oral administration coupler 100 or female connector FC relative to the other to provide engagement therebetween, the female connector FC can optionally be generally axially advanced relative to the coupling 134 so that the coupler 100 becomes removably engaged with the syringe S. In example forms, the flexible fingers 150 generally flex outwardly such that the female connector FC can become engaged with the connector 134, for example, thereby causing the ribs R to become engaged with the internal threaded portion 142. In example forms, the female connector FC and the ribs R thereof being generally axially advanced relative to the fingers 150 causes the ribs R to become engaged with the threaded portion 142 of the fingers 150, and wherein further axial advancement of the female connector FC enables the ribs R to cause outward flexure of the fingers 150, and then back to a neutral state, for example, wherein the ribs are generally removably engaged with the threaded portion 142. In example forms, to remove the coupler 100 from the female connector FC of the syringe S, one of the coupler 100 or the female connector FC is generally rotated relative to the other of the coupler 100 or female connector FC.

Figure 12:
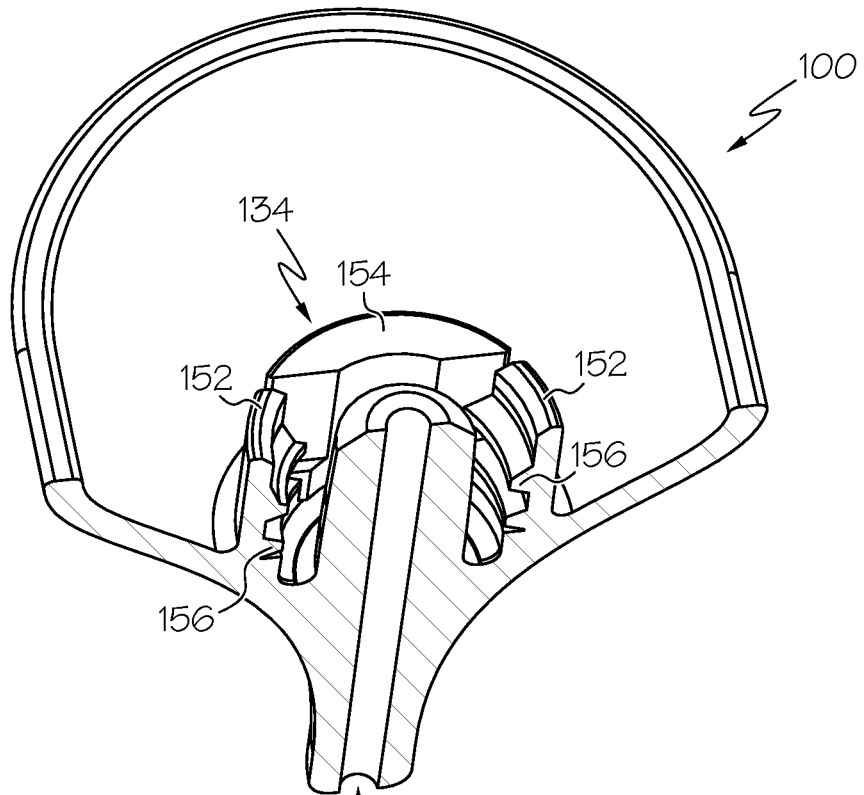
FIG. 12 shows a cross-sectional view of the oral administration coupler of FIG. 11 taken along line 12-12.
Figure 13:
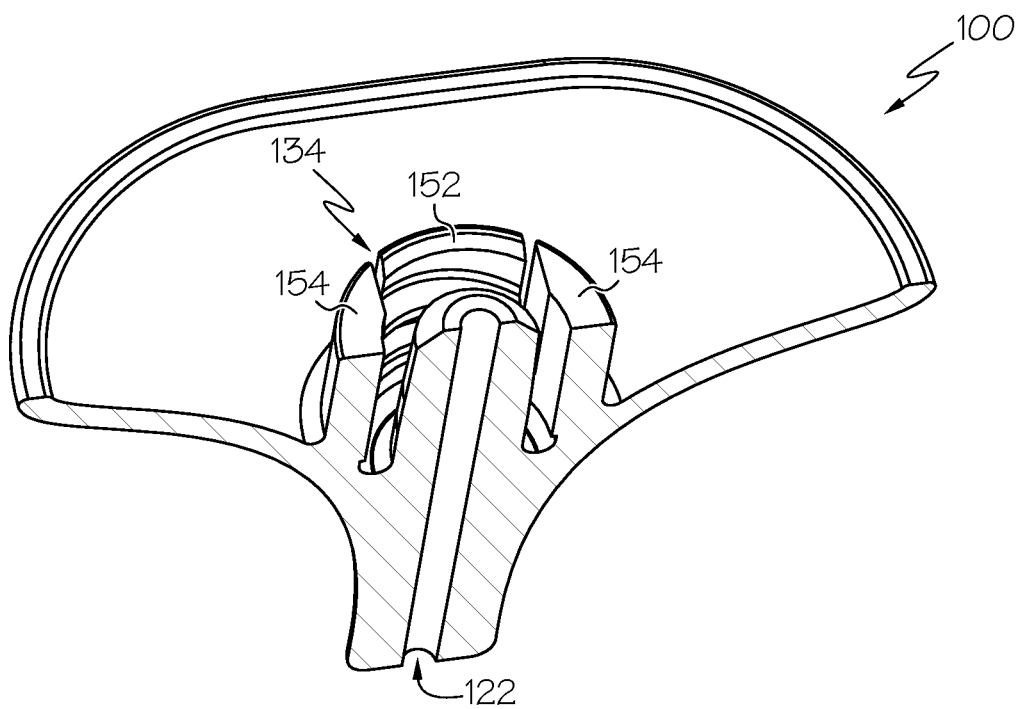
FIG. 13 shows a cross-sectional view of the oral administration coupler of FIG. 11 taken along line 13-13.

FIGS. 11-15 show the oral administration coupler 100 having yet another modified ENFit compatible coupling. As depicted, the coupling 134 comprises a locking hub connection whereby the female connector FC is substantially permanently connected once coupled therewith. For example, the coupling preferably comprises a pair of clips 152 extending outwardly on opposite sides of each other, and the sides generally adjacent the clips comprise substantially rigid supports or guide tabs 154. As shown in FIG. 12, the clips generally comprise at least one or more ribs or threads 156 on an internal portion thereof, which preferably provide for interengagement with the ribs R of the female coupling FC. However, as shown in FIG. 13, the guide tabs 154 do not comprise any threads and are substantially thicker than the clips. Thus, during engagement of the female coupling FC with the coupler 100, the ribs R are generally oriented to interengage with the threads of the clips. Preferably, the clips are at least partially flexible such that the ribs R of the female coupling FC pass by the threads of the clips when the clips are forced to flex outwardly. Once the coupling is coupled to the female coupling FC, the coupling is prevented from rotating due to the guide tabs interfering with the ribs R of the female coupling FC. Furthermore, the clips are at least partially rigid such that the female connector is generally prevented from being pulled apart from the female coupling FC.

Figure 14:
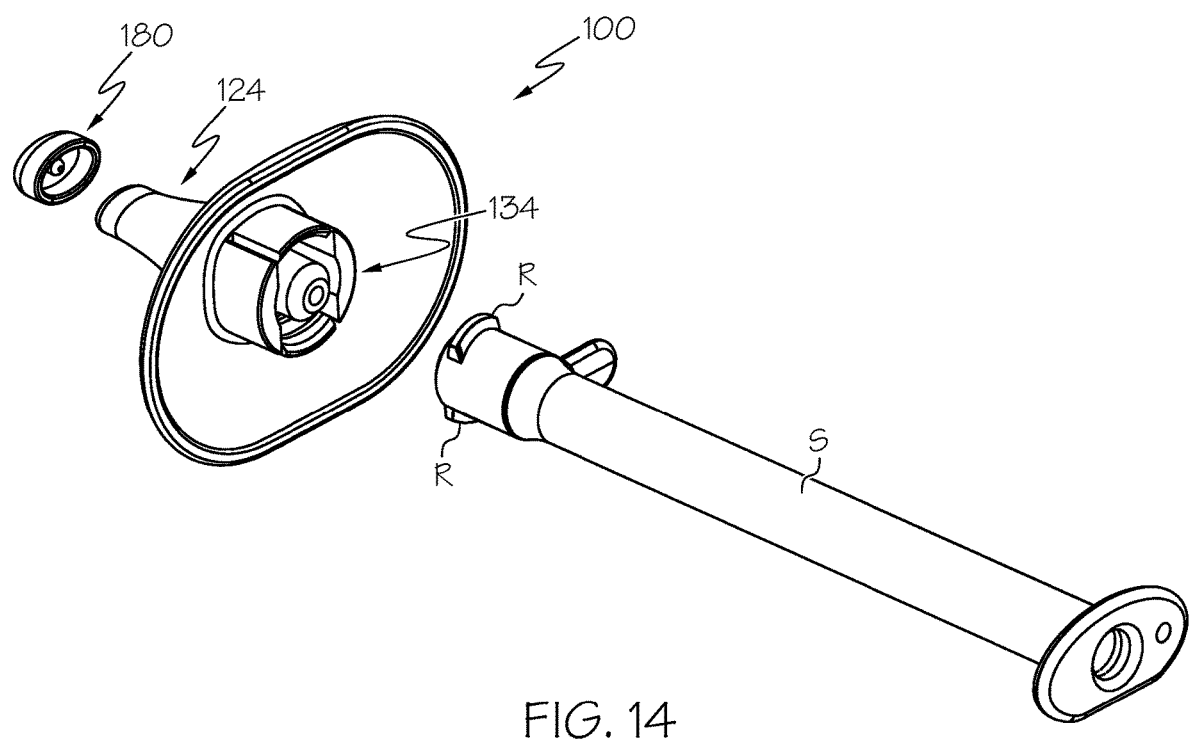
FIG. 14 shows a rear perspective assembly view of the oral administration coupler of FIG. 11 positioned between a syringe and a cap, the syringe being permanently engageable with the oral administration coupler and the cap being removably engageable with the oral administration coupler.
Figure 15:
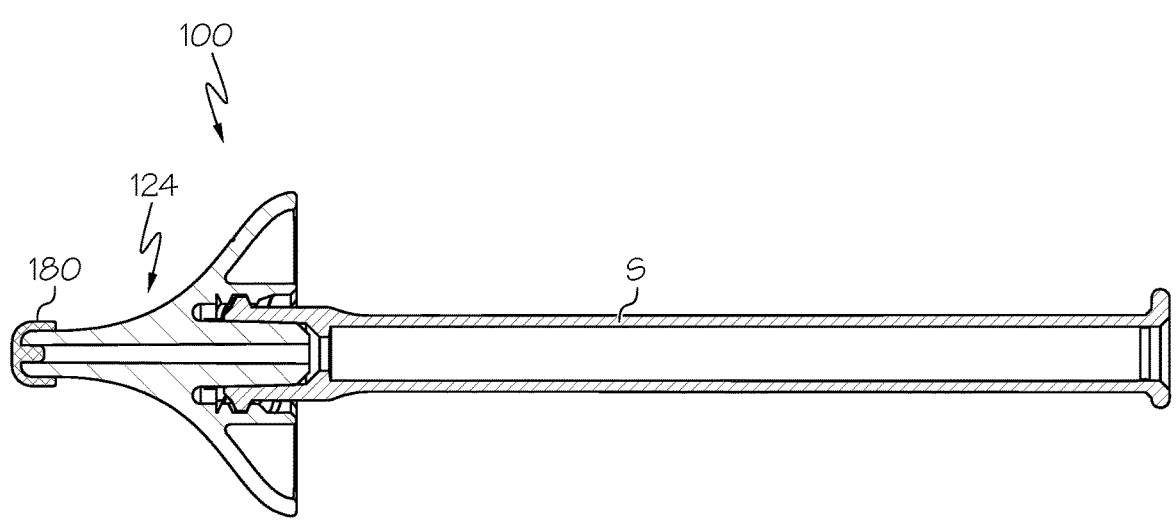
FIG. 15 shows a cross-sectional view of the oral administration coupler assembled with the syringe and cap as shown in FIG. 14.
Figure 16:
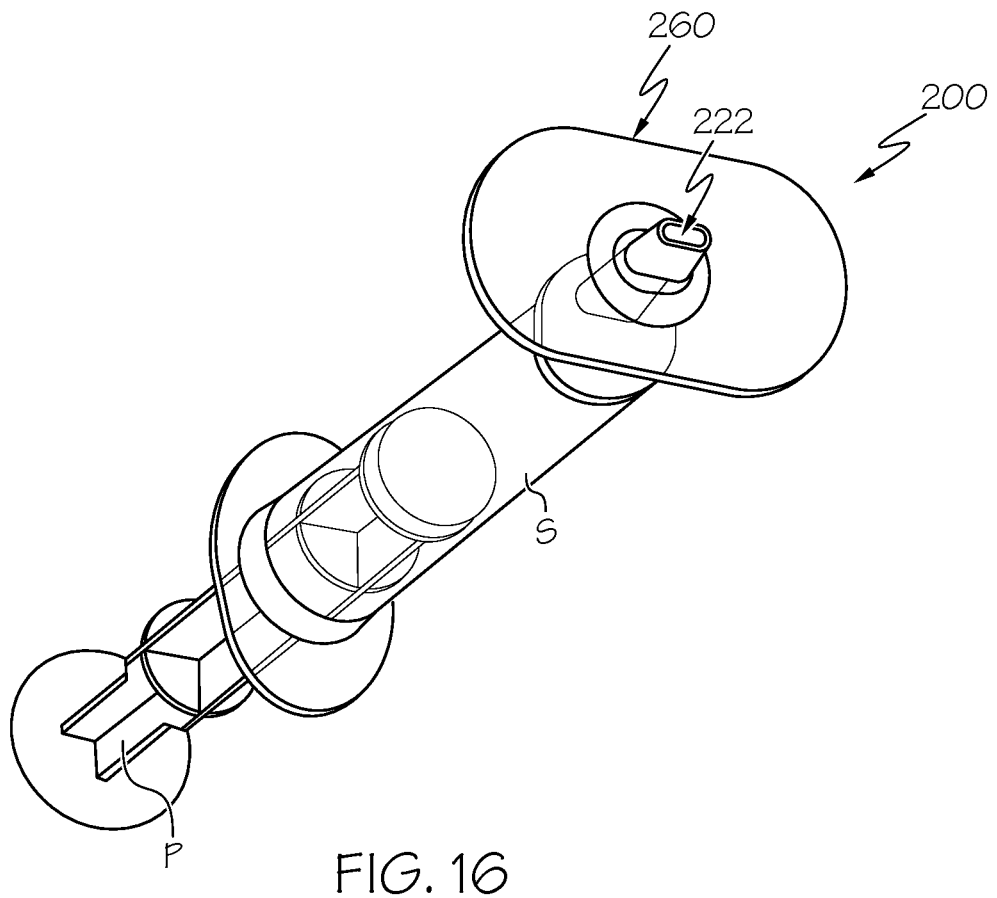
FIG. 16 shows an oral administration coupler assembled with a syringe according to another example embodiment of the present invention.
Figure 17:
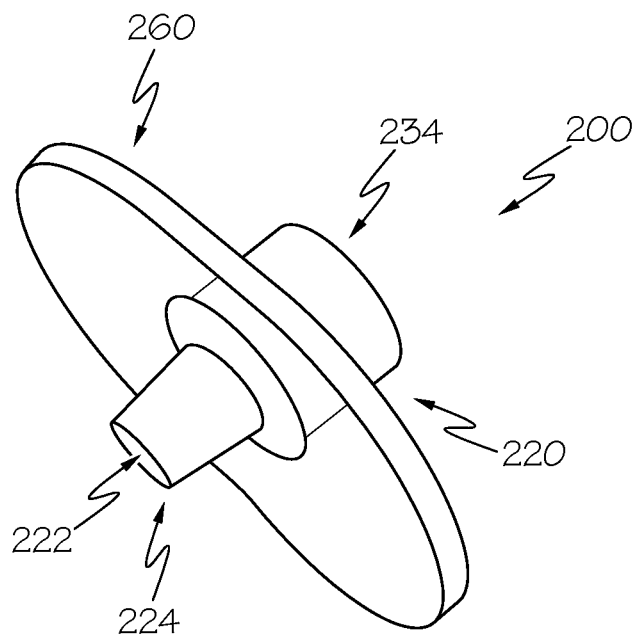
FIG. 17 shows a top perspective view of the oral administration coupler shown in FIG. 16.
Figure 18:
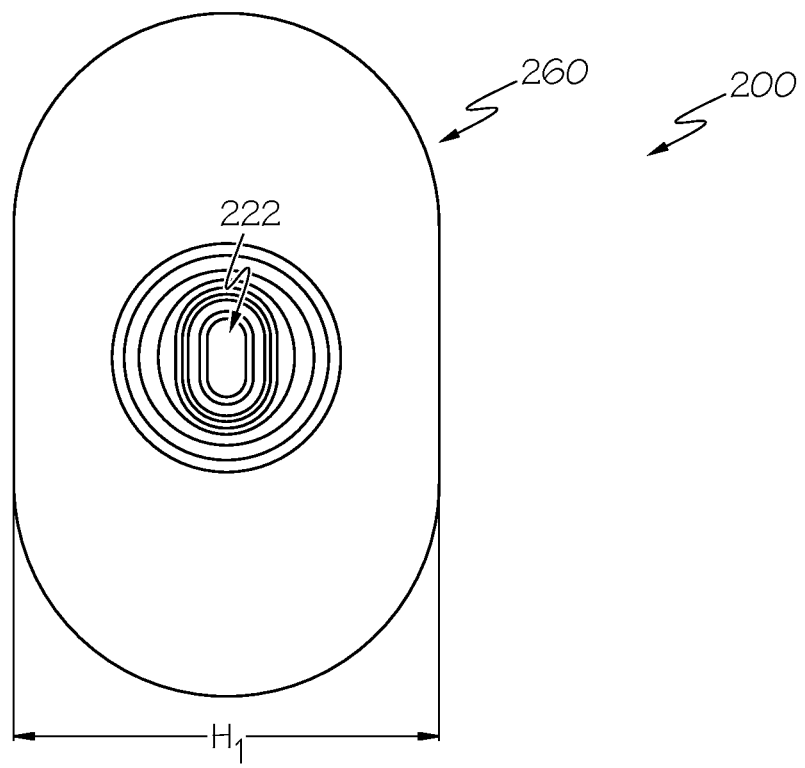
FIG. 18 shows a top plan view of the oral administration coupler of FIG. 16.

Optionally, as depicted in FIGS. 14-15, the distal end of the coupling may be provided with a cap or closure 180. In example forms, the closure 180 is generally shaped similarly to the distal end of the coupling and comprises a nipple therein for extending within the lumen 122 of the coupling. Preferably, the closure 180 may be shaped and sized as desired. Typically, the closure 180 will generally be shaped and sized to provide a generally tight yet removable fit with the distal end of the coupling, for example, which may be in the form a friction fit connection, a twist-on and/or snap-on, or other connections as desired. According to some example forms, the closure 180 may be permanently coupled with the distal end of the coupling once coupled thereto. In some example forms, the closure 180 is tethered with the coupling but without interfering with the administration of fluids from the distal end thereof. As depicted, the closure 180 is a separate piece. Preferably, the closure prevents fluids that may be within the lumen of the coupling from exiting therefrom.

In further example embodiments, the ENFit compatible coupling 134 that is configured for the push-on or snap-fit coupling engagement (e.g., having the fingers 150) or the locking hub connection (e.g., having the clips 152 and the tabs 154) can be used with a variety of other enteral delivery couplers or other enteral connectors or couplings as desired. For example, according to some example forms, the coupling 134 configured for push-on coupling engagement or the locking hub connection (as shown in FIGS. 10-15) can be configured for use with enteral couplings, connectors or other devices or members configured for engagement with an ENFit female connector FC. Thus, alternative aspects of the invention include the coupling itself, apart from the oral administration coupler, according to any of the disclosed example embodiments, which coupling is adaptable for use in connection with various other forms of fluid delivery devices, in addition to an oral administration coupler as depicted.

Figure 19:
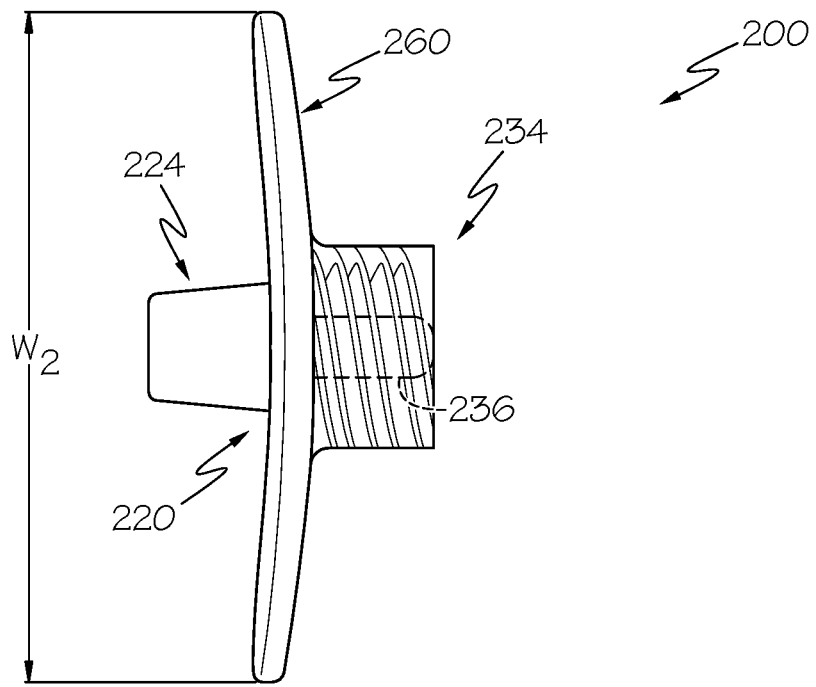
FIG. 19 shows a side plan view of the oral administration coupler of FIG. 16.

FIGS. 16-19 show an oral administration coupler according to another example embodiment of the present invention. As depicted, the oral administration coupler 200 generally comprises a central fluid transfer member 220 having an oral administration applicator 224 and an ENFit compatible coupling 234, and whereby a lumen 222 is generally defined therein and extends between the ends thereof. A flange 260 generally extends outwardly from the central fluid transfer member and generally between the oral administration applicator 224 and the coupling 234. In example embodiments, the outer periphery 262 of the flange 260 is generally non-circular, for example, having two generally opposite radiused ends defining a width $W_2$ and a height $H_1$. In example forms, the width $W_2$ is at least slightly larger than the height $H_1$. According to one form as depicted in FIG. 19, the flange 260 is generally at least partially curved towards the end of the central fluid transfer member 220 having the oral administration applicator 224. Optionally, the flange 260 can be shaped as desired.

Figure 20:
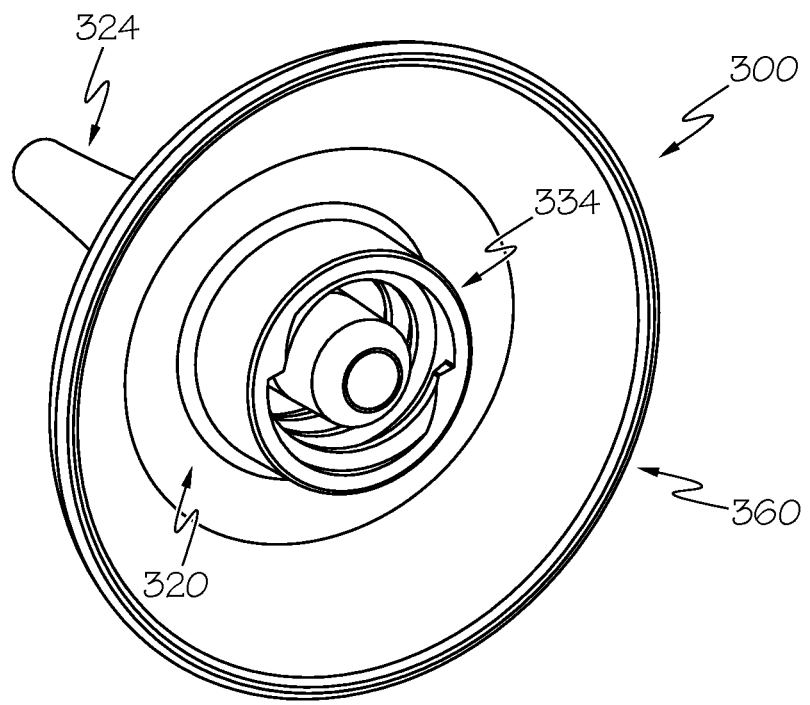
FIG. 20 shows a rear perspective view of an oral administration coupler according to another example embodiment of the present invention.
Figure 21:
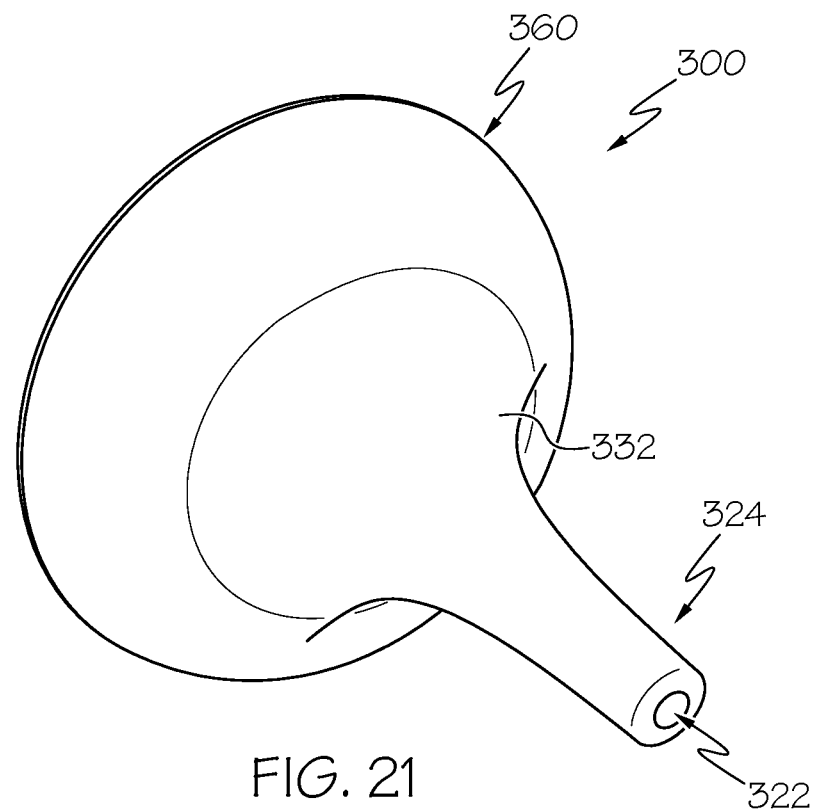
FIG. 21 shows a front perspective view of the oral administration coupler of FIG. 20.

FIGS. 20-21 show an oral administration coupler 300 according to another example embodiment of the present invention. As depicted, the oral administration coupler 300 generally comprises a central fluid transfer member 320 having an oral administration applicator 324 and an ENFit compatible coupling 334. A lumen 322 is formed within the central fluid transfer member and extends entirely through the applicator 324 and the coupling 334. A flange 360 generally extends outwardly from the central fluid transfer member and generally between the oral administration applicator 224 and the coupling 234. In example embodiments, the outer periphery 262 of the flange 260 is generally circular in shape. Similarly, the oral administration applicator 324 is generally cylindrical in shape and comprises a generally circular cross-section. In example forms, a radiused transition 332 is provided for defining a smooth transition between the oral administration applicator 324 and the outer surface of the flange 260. Optionally, as shown in FIGS. 22-24, the oral administration coupler 300 can comprise one or more vents 367 to mitigate potential choking hazards and to act as a channel for permitting fluids to flow therethrough, for example, which may be otherwise contained within the coupler 300. In example forms, two vents 367 are generally positioned on opposite sides of the central fluid transfer member and generally extend entirely through the flange 360.

FIGS. 25-28 shows an oral administration coupler 400 according to another example embodiment of the present invention. As depicted, the oral administration coupler 400 is generally elongate and extends generally linearly from a first end to a second end. For example, as similarly described above, the coupler 400 comprises an oral administration applicator 424 for orally administering the fluids and an ENFit compatible coupling 434 for coupling with the female connector FC of the syringe S. A lumen (unshown) extends entirely through the coupler 400, for example, to allow fluids from the syringe S to be delivered to the human or animal patient. In example forms, the applicator 424 is generally elongate and has a substantially circular cross-sectional shape.

Figure 25:
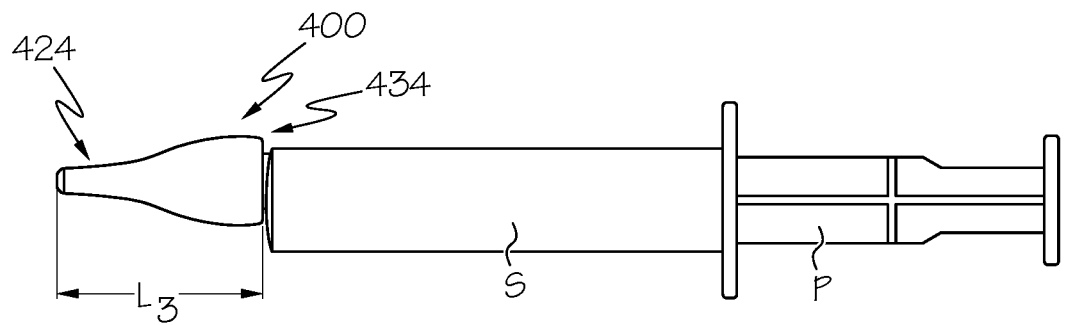
FIG. 25 shows a side view of an oral administration coupler according to another example embodiment of the present invention, and showing the coupler removably mounted to a syringe.
Figure 26:
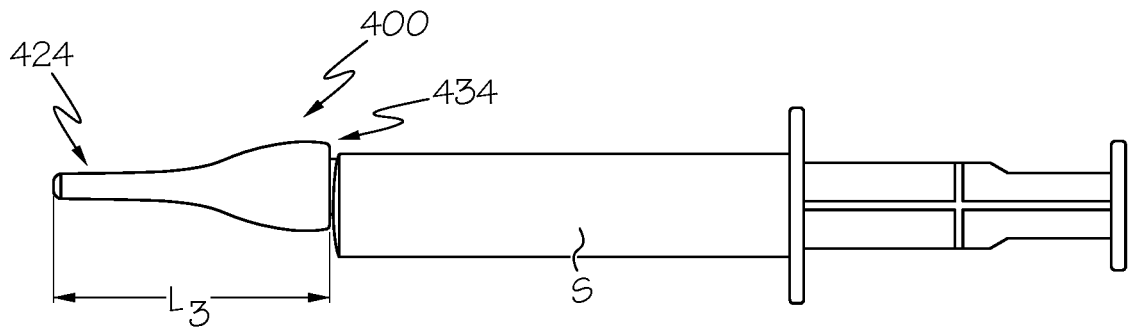
FIG. 26 shows a side view of an oral administration coupler according to another example embodiment of the present invention, and showing the coupler removably mounted to a syringe.
Figure 27:
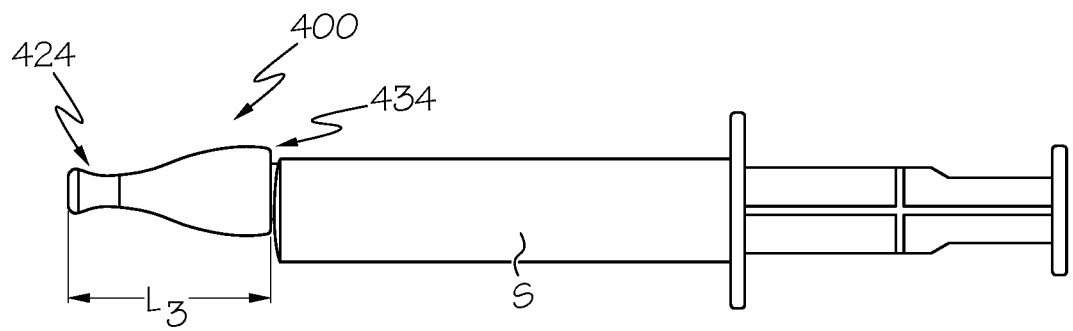
FIG. 27 shows a side view of an oral administration coupler according to another example embodiment of the present invention, and showing the coupler removably mounted to a syringe.
Figure 28:
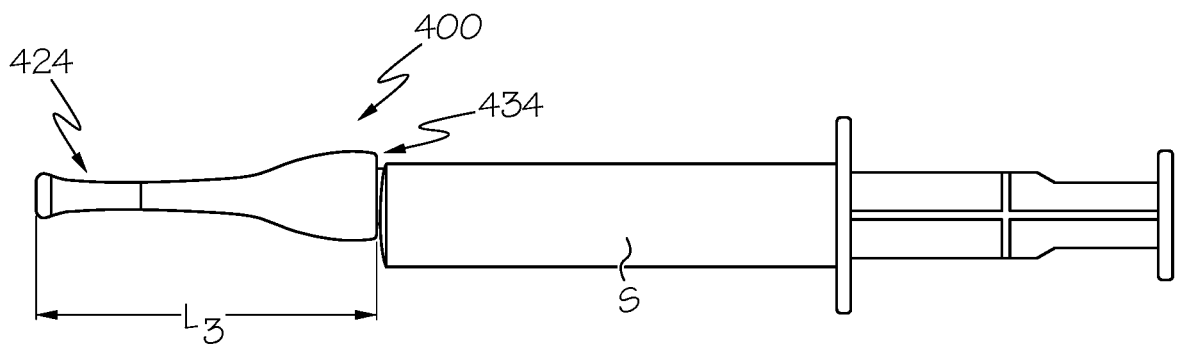
FIG. 28 shows a side view of an oral administration coupler according to another example embodiment of the present invention, and showing the coupler removably mounted to a syringe.

In example forms, the coupler 400 defines a length $L_3$, which can preferably be sized accordingly. For example, the length $L_3$ of the coupler 400 shown in FIG. 25 is about 30 millimeters, the length $L_3$ of the coupler 400 shown in FIG. 26 is about 45 millimeters, the length $L_3$ of the coupler 400 shown in FIG. 27 is about 30 millimeters, and the length $L_3$ of the coupler 400 shown in FIG. 28 is about 50 millimeters. Optionally, the length $L_3$ can be chosen as desired, for example, which is generally between about 15 millimeters to about 60 millimeters, more preferably between about 30 millimeters to about 50 millimeters. In example embodiments, the length $L_3$ is generally at least about 1.25-1.75 times larger than the width or diameter of the coupling 434. In some example forms, the length $L_3$ is generally 2-3 times larger than the diameter of the coupling 434.

As depicted in FIGS. 25-26, the applicator 424 comprises a generally elongate post-like nozzle, which generally comprises a substantially similar cross-section until transitioning to the coupling 424, for example, where the diameter of the cross-section substantially increases. However, as depicted in FIGS. 27-28, the applicator 424 generally comprises a horn-shaped tip wherein the diameter of the cross-section at the end of the applicator 424 (e.g., first end) is generally larger than the diameter of the cross-section at a middle portion or midsection of the applicator 424. Optionally, the applicator 424 can be shaped and sized as desired.

Figure 29:
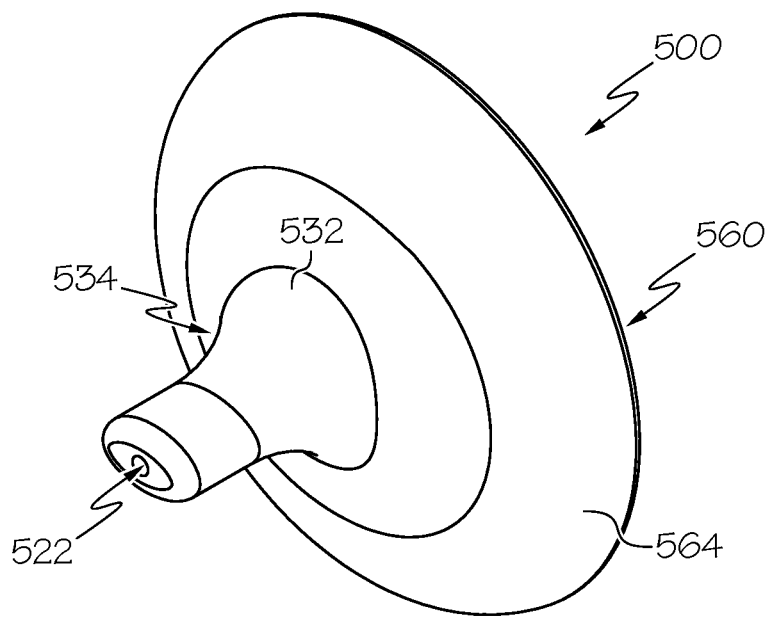
FIG. 29 shows a front perspective view of an oral administration coupler according to another example embodiment of the present invention.
Figure 30:
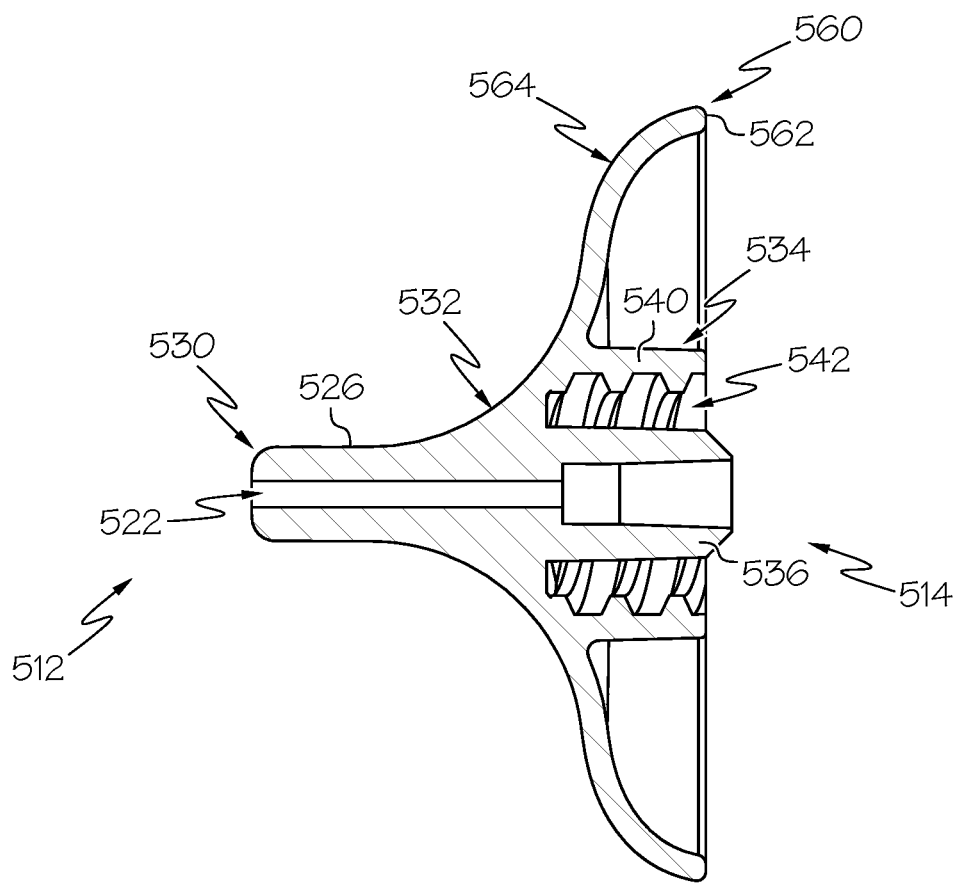
FIG. 30 shows a cross-sectional view of the oral administration coupler of FIG. 29.
Figure 31:
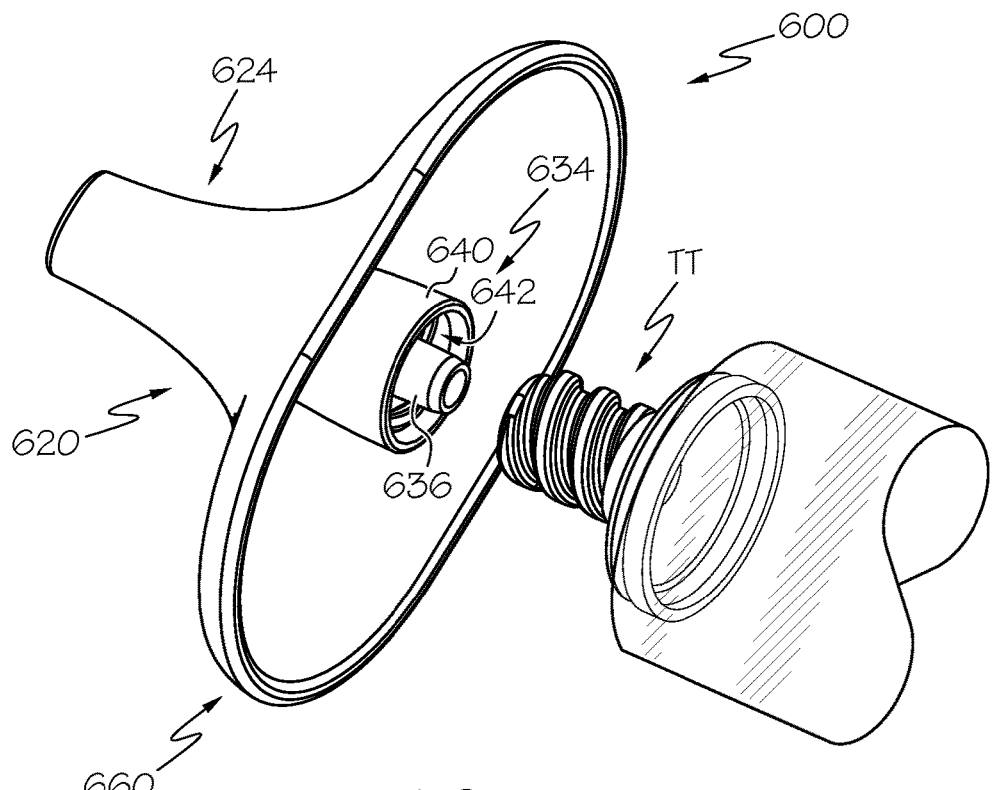
FIG. 31 shows a rear perspective assembly view of an oral administration coupler and a syringe according to another example embodiment of the present invention.
Figure 32:
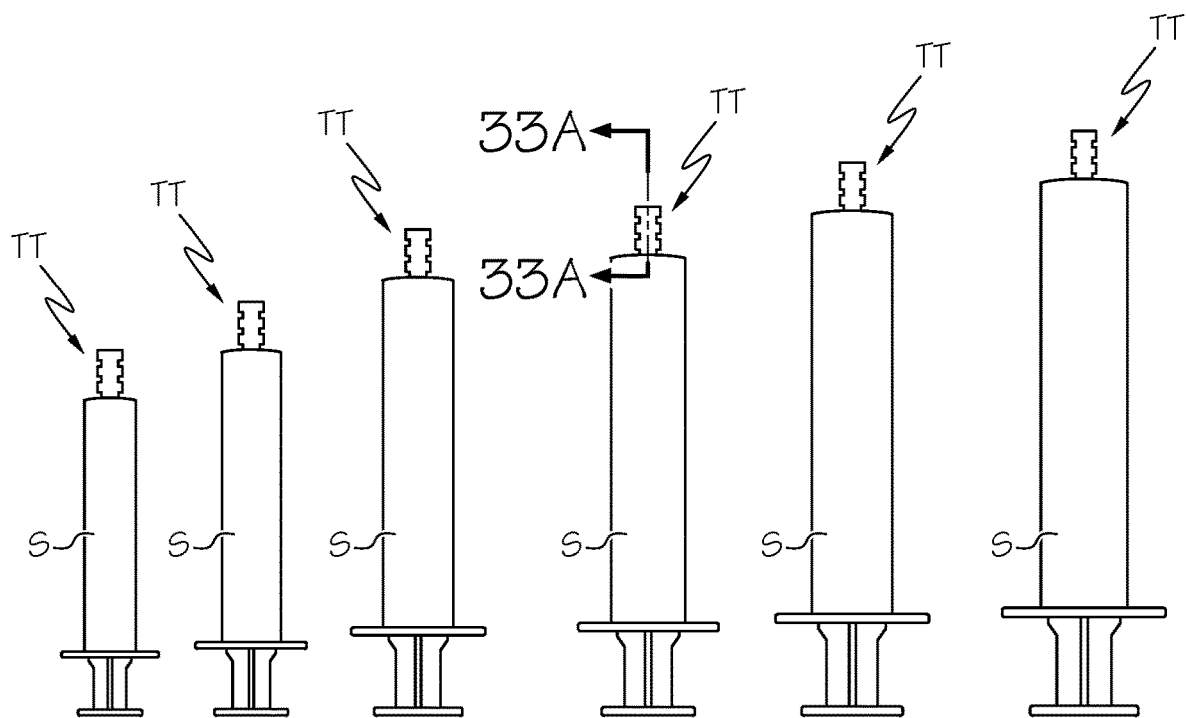
FIG. 32 shows a plurality of syringes for use with the oral administration coupler shown in FIG. 31.

FIGS. 29-30 show an oral administration coupler 500 according to another example embodiment of the present invention. As depicted, the coupler 500 is generally similar to the coupler 10 as described above. In example forms, the coupler 500 generally comprises a central fluid transfer member 520 having an oral administration applicator 524 and an ENFit compatible coupling 534. Preferably, a lumen 522 is generally defined within the applicator 534 and the coupling 534, and extends entirely between the ends thereof. A flange 560 generally extends outwardly from the central fluid transfer member and generally between the oral administration applicator 524 and the coupling 534. In example embodiments, the outer periphery 562 of the flange 560 is generally circular, for example, which is substantially similar to the flange 60 of the coupler 10 (see FIGS. 1-7). Furthermore, as similarly described above, the applicator 524 is generally in the form of an irregular or asymmetric nipple, which is generally duckbilled in shape and having a generally non-circular or oval cross-section. Optionally, the applicator can be shaped as desired. Similarly to the flange 60, the flange 560 comprises a radiused transition 532 formed with the oral delivery applicator 524, and an outer portion of the flange 560 generally comprises a radiused surface profile 564 that extends to the outer periphery 562. Preferably, the flange 560 is generally substantially symmetrical and comprises a substantially smooth and radiused outer surface.

According to additional example embodiments, the oral administration coupler can be formed such that a threaded syringe tip is capable of interengagement therewith. For example, FIGS. 31-34 show an oral administration coupler 600 that is generally substantially similar to the couplers as described above, for example, which generally comprises a central fluid transfer member 620 comprising an oral administration applicator 624, a coupling 634, and a flange 660 generally outwardly extending from the central fluid transfer member 620. Preferably, the coupling 634 comprises a central port 636 defining a lumen 622 extending through the central fluid transfer member 620, and a collar 640 is generally positioned to substantially surround the central port 636. Preferably, the collar 640 comprises a threaded internal portion 642 for providing removable engagement with helical threads T of a threaded tip TT of a syringe (see also FIGS. 31-34). According to some example forms, the threads T of the threaded tip TT comprise a thread pitch TP of about 2.45 millimeters and an outer diameter $D_3$ of about 6.657 millimeters (see FIG. 33A), and the threaded internal portion of the coupling preferably has dimensions to provide a complementary fit therewith. Optionally, other dimensions may be provided as desired. As depicted in FIG. 34, the volume path $V_1$ defined between the coupling and the threaded tip TT is generally between about 0.005-0.10 ml, more preferably about 0.02 ml.

Figure 35:
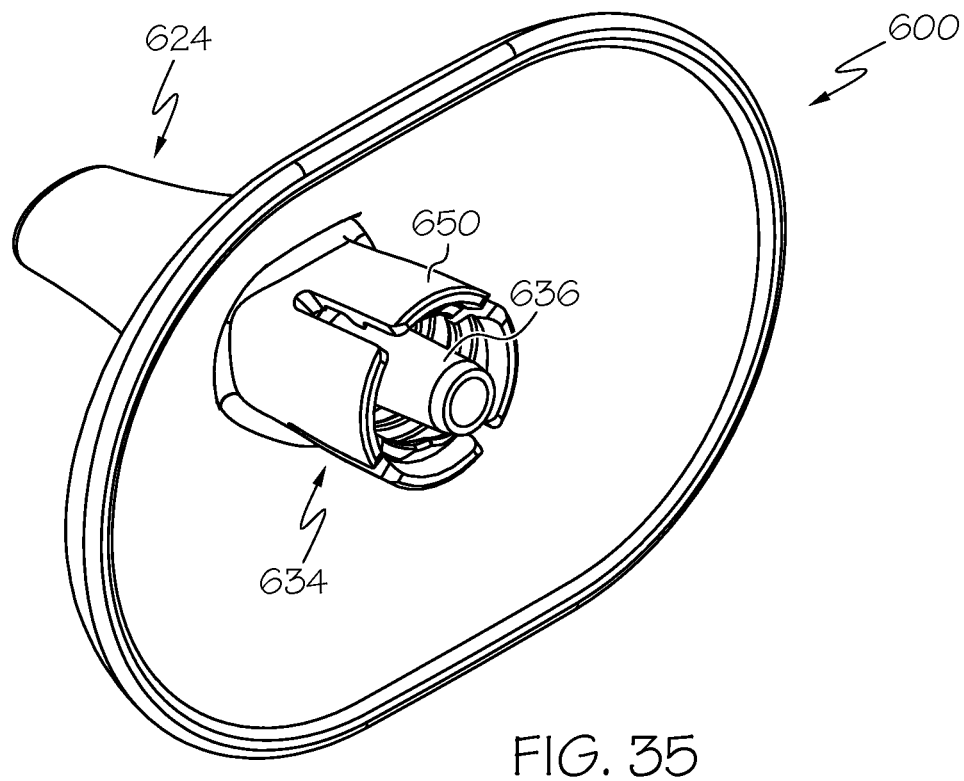
FIG. 35 is a rear perspective view of an oral administration coupler according to another example embodiment of the present invention.

FIG. 35 shows a coupler 600 according to another example embodiment of the present invention. As depicted, the coupler 600 preferably comprises about four clips 650 and wherein the internal portions thereof comprises a threaded portion for interengagement with the threads T of the threaded tip TT. According to some example forms, the coupler 600 is configured to be coupled to the threaded tip TT by generally axially moving one of the coupling or threaded tip TT towards the other. During movement therebetween, the clips 650 are capable of generally flexing outwardly to allow for the threaded internal portion of the coupling to pass over the threads T of the threaded tip. To disengage the coupling from the threaded tip TT, the coupling 600 is generally unscrewed from the threaded tip.

Figure 36:
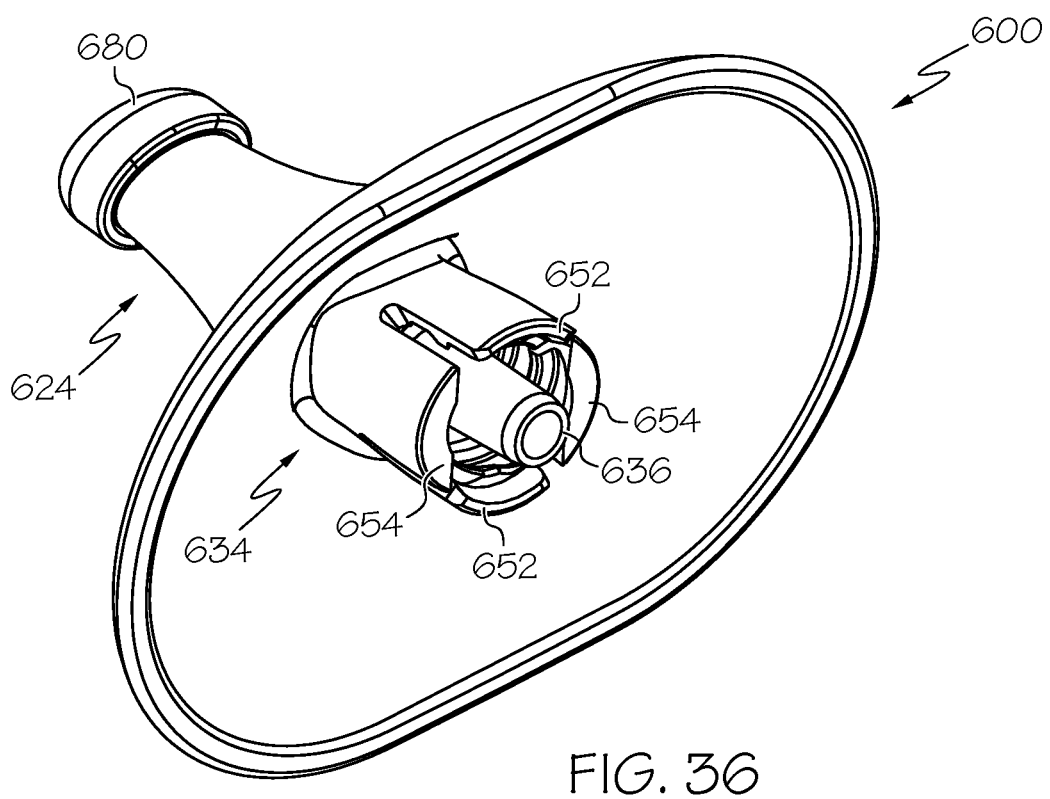
FIG. 36 is a rear perspective view of an oral administration coupler according to another example embodiment of the present invention, and showing a cap removably attached to a portion thereof.

FIG. 36 shows a coupler 600 according to another example embodiment of the present invention. As shown, the coupler 600 comprises locking clips 652 formed near the threaded internal portion of the coupling such that the coupling is incapable of being removed from the threaded tip TT of the syringe. For example, once the threaded tip TT is inserted within the coupling 634 and the threads or interengagement features therein interengage with the threads T of the threaded tip TT, the coupling is substantially permanently engaged with the threaded tip U. As similarly described above, the clips 652 are generally at least partially flexible and the guide tabs 654 are generally rigid and comprise a greater thickness than the clips. Optionally, as depicted in FIG. 36, a cap or closure 680 may be provided with the coupling such that fluids a prevented from flowing from the end of the coupling. Furthermore, as recited above, the cap 680 may be in a variety of shapes and forms to removably or permanently couple with the distal end of the coupling. According to some example forms, the cap is generally a separate piece which may be separable from the coupler. According to other example forms, the closure 680 is tethered to the coupler 600. According to some example forms, the tether does not inhibit the administration of fluids orally.

In example forms, the oral administration coupling is generally formed from a rigid material (>700 MPA as per the ISO standard). Optionally, the coupling may be formed from a flexible, elastomeric material. Further optional, the oral administration coupling can be formed from two or more materials, for example, at least one rigid material and at least one flexible, elastomeric material. In some example forms, the coupling can be formed from materials of one or more colors and/or may be at least partially translucent or clear, for example, such that the fluid or nutrients flowing therethrough are visible to the human eye. Optionally, the coupling can be in the formed from light protecting materials, for example, reflecting or blocking UV or other wavelengths to reduce or eliminate damage to contents by light. As depicted in the figures, the coupling is generally linear (e.g., straight). Optionally, the coupling can be curved, angled, or otherwise shaped as desired. Optionally, an end portion of the coupling (e.g., applicator) may be shaped to be generally round, oval, crescent, rectangular, flat, radiused, other otherwise shaped as desired. Optionally, the end portion of the coupling may be shaped similarly to an enteral only syringe tip.

Figure 37:
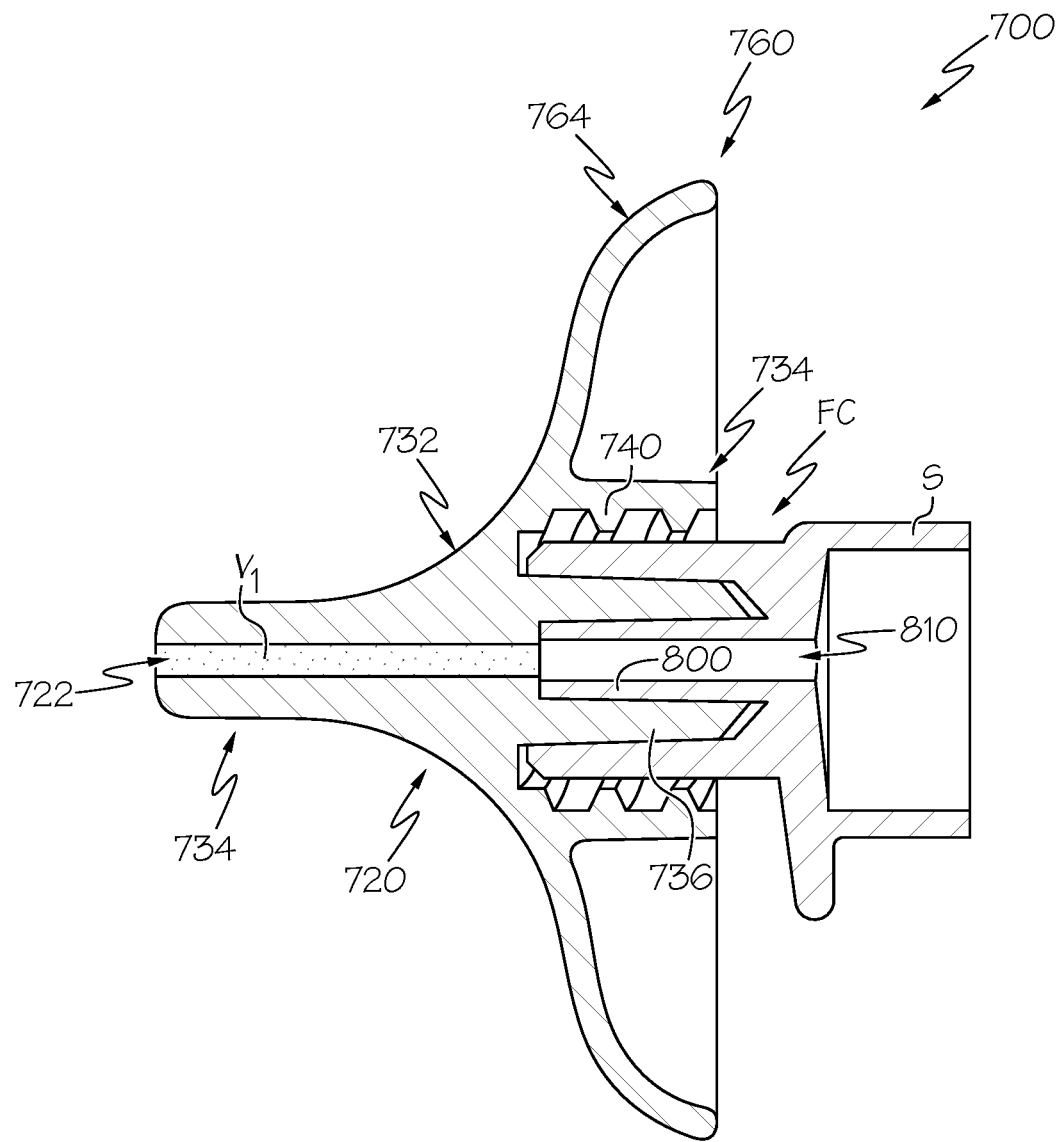
FIG. 37 is a cross-sectional view of an oral administration coupler removably coupled to a syringe having a lumen extension tip within the female connector thereof according to another example embodiment of the present invention.

According to additional example embodiments of the present invention, the coupling may be provided as an accessory to a bottle or variable-volume container, for example, as disclosed in U.S. patent application Ser. No. 13/191,721, the entirety of which is incorporated herein by reference. Optionally, according to additional example embodiments of the present invention, the oral administration coupling as shown throughout the figures can be provided as an accessory to a variable-volume syringe comprising a modified ENFit coupling comprising a dosing control coupling, for example, as disclosed in U.S. Provisional Patent Application Ser. No. 62/207,120, the entirety of which is incorporated herein by reference. According to example forms, the dosing control coupling preferably provides for a more accurate output of fluids from the syringe relative to the volume of fluids filled within the syringe, for example, so that the administered dose delivered to the patient is substantially accurate. For example, as depicted in FIG. 37, the syringe S comprises a female connector FC, which further comprises a lumen extension tip 800 that is generally axially aligned with the female connector FC and comprising a lumen 810 therein for communicating with the internal cavity or chamber of the variable volume container or syringe S. As such, the female connector FC is generally removably coupled to an ENFit compatible coupling 734 of an oral administration coupler 700. As depicted, the oral administration coupler is generally substantially similar to the oral administration coupler 10 as described above, for example, and comprising a fluid transfer member 720 extending between a first end and a second end, and wherein the first end comprises an oral administration applicator 734 and the second end comprises the ENFit compatible coupling 734 for providing engagement with the female connector FC of the syringe (and the lumen extension tip 800) axially extending therein. Furthermore, a flange 760 generally extends outwardly in a circumferential manner to define a generally cylindrical shape.

In example forms, the lumen extension tip 800 preferably generally extends entirely within the lumen of the port 736, and comprises the lumen 810 therein for generally communicating with the lumen 722 that is generally axially centered within the generally linear extension of the applicator 734. Preferably, with the lumen extension tip 800 provided within the female connector FC, the volume equivalence (see FIG. 7) generally becomes less important, for example, since the volume of the lumen 722 is substantially decreased by introduction of the lumen extension tip 800 within the lumen of the port 736. Thus, according to example forms, the size of the lumen 722 that is not occupied by the lumen extension tip 800 (e.g., $V_1$) can be varied, for example, between about 0.0005 mL to about 0.02 mL, more preferably between about 0.0015 mL to about 0.015 mL, for example about no more than 0.01 mL according to one example embodiment. As similarly described with respect to FIG. 7 and the coupler 10, preferably one or more dimensions of the coupler 700 can be configured as desired, for example, the diameter D1, the length L1, the width W1, the thickness T1, the length L2 and the diameter D2.

In additional example embodiments, the present invention relates to a method of designing a fluid delivery device comprising calculating a volume of at least a portion of a fluid delivery path of a first fluid delivery device; and designing a fluid delivery path of a second fluid delivery device to substantially match the fluid delivery path volume of the first fluid delivery device. In example forms, the first fluid delivery device comprises a pharmacy coupler for transferring fluids from a container to a syringe. Generally, the second fluid delivery device comprises an oral administration coupler for delivering fluids from a syringe to a cheek area of a child or infant.

While the invention has been described with reference to preferred and example embodiments, it will be understood by those skilled in the art that a variety of modifications, additions and deletions are within the scope of the invention, as defined by the following claims.

What is claimed is:

1. An oral administration coupler for delivering fluids from a syringe to a child or infant, the syringe comprising a connector, the oral administration coupler comprising:

a conduit extending from a first end to a second end along an elongate axis, the first end comprising a generally elongate member for oral insertion to deliver fluids to the child or infant, and the second end comprising a compatible fitting for removable engagement with the connector of the syringe; and a flange projecting outwardly from the conduit in an oblique direction relative to the elongate axis towards the second end, wherein a transition between the generally elongate member and the flange comprises a concavely radiused surface profile, wherein an outer portion of the flange adjacent the second end comprises a convexly radiused surface profile extending towards the second end and generally terminating at an outer periphery of the flange.

2. The oral administration coupler of claim 1, wherein the elongate member of the first end is substantially rigid and comprises an oval cross section.

3. The oral administration coupler of claim 1, wherein the compatible fitting of the second end comprises an ENFit compatible fitting, the ENFit compatible fitting comprising an outer circumferential collar having threads defined on an internal portion thereof, and a transfer port generally axially extending relative to the collar and comprising the conduit extending therethrough.

4. The oral administration coupler of claim 1, wherein the flange is generally circular in shape, and wherein a smoothly radiused transitional surface is provided from the generally elongate member, along the convexly radiused surface profile, and to the outer periphery of the flange.

5. The oral administration coupler of claim 1, further comprising one or more vents or openings defined in the flange.

6. The oral administration coupler of claim 4, wherein the outer peripheral portion of the flange defines a diameter of between about 20-40 millimeters.

7. The oral administration coupler of claim 6, wherein the outer peripheral portion of the flange defines a diameter of about 32.835 millimeters.

8. The oral administration coupler of claim 1, wherein the conduit extends a distance between the first and second ends of between about 15-35 millimeters.

9. The oral administration coupler of claim 8, wherein the conduit extends a distance between the first and second ends of about 20.35 millimeters.

10. The oral administration coupler of claim 1, wherein a volume defined within the connector and within the conduit of the coupler is generally between about 40 mm$^3$ to about 70 mm$^3$.

11. The oral administration coupler of claim 1, wherein a volume defined within the connector and within the conduit of the coupler is about 60 mm$^3$.

12. The oral administration coupler of claim 3, wherein the syringe comprises a female connector, the female connector comprising a lumen extension tip axially extending therein and comprises a lumen therein and in communication with an internal chamber of the syringe, and wherein when the female connector is engaged with the ENFit compatible fitting of the second end of the conduit, the lumen extension tip fully extends within a conduit of the transfer port.

13. The oral administration coupler of claim 12, wherein a volume defined within the conduit of the coupler is substantially reduced by the conduit of the transfer port being occupied by the lumen extension tip of the female connector.

14. The oral administration coupler of claim 13, wherein the volume defined within the conduit is generally no more than about 0.01 mL.

15. The oral administration coupler of claim 1, wherein the flange is substantially large such that choking risks are mitigated.

16. The oral administration coupler of claim 1, wherein the elongate member of the first end comprises a circular cross section defining a width of between about 4.5-6 millimeters.

17. An oral administration coupler for orally delivering fluids from a syringe to a child or infant, the oral administration coupler comprising:
a central fluid transfer member comprising a first end, a generally opposite second end and an outer periphery, the first end of the central fluid transfer member comprising an oval cross section having a width of between 3.5-6.5 millimeters and a thickness of between 2-5 millimeters;
a lumen defined within the central fluid transfer member and extending from the first end to the second end along an elongate axis, the elongate axis centrally positioned relative to the central fluid transfer member; and
a flange generally positioned between the first and second ends of the fluid transfer member, the flange generally extending outwardly from an outer periphery of the central fluid transfer member,
wherein a concavely radiused transition is provided from an outer periphery of the central fluid transfer member to the flange to provide for a comfortable contact surface with the child or infant when the first end of the central fluid transfer member is orally inserted within a mouth thereof, the radiused transition configured so as to provide a continuous and smooth transitional surface between the outer periphery of the central fluid transfer member and the flange.

18. The oral administration coupler of claim 17, wherein the first end of the central fluid transfer member comprises a generally elongate stem having an oval cross-sectional shape.

19. The oral administration coupler of claim 18, wherein the generally elongate stem is generally duckbilled in shape.

20. The oral administration coupler of claim 17, wherein the second end of the central fluid transfer member comprises an ENFit compatible coupling having a centrally-positioned transfer port and an outer collar comprising an internally threaded portion.

21. The oral administration coupler of claim 20, wherein the ENFit compatible coupling is configured for removable engagement with a female connector of a syringe.

22. The oral administration coupler of claim 17, wherein the second end of the central fluid transfer member comprises a coupling having a centrally-positioned transfer port and an outer collar comprising an internally threaded portion.

23. The oral administration coupler of claim 22, wherein the coupling is configured for removable engagement with a syringe having a threaded tip.

24. The oral administration coupler of claim 23, wherein the threaded tip generally comprises an outer diameter and a thread pitch, the outer diameter being between about 4 millimeters to about 9 millimeters and the thread pitch being between about 1 millimeter to about 5 millimeters.

25. The oral administration coupler of claim 24, wherein the outer diameter is about 6.657 millimeters and the thread pitch is about 2.450 millimeters.

26. The oral administration coupler of claim 17, wherein an outer peripheral portion of the flange defines a diameter of about 32.835 millimeters.

27. An oral administration coupler for delivering fluids from a syringe to a child or infant, the syringe comprising a fully threaded tip, the fully threaded tip comprising an outer diameter of between about 6 millimeters to about 7 millimeters and a thread pitch of between about 2 millimeters to about 3 millimeters, the oral administration coupler comprising:
a conduit extending from a first end to a second end along an elongate axis, the first end comprising a generally elongate oral delivery applicator for oral insertion to deliver fluids to the child or infant, and the second end comprising a coupling for removable engagement with the fully threaded tip of the syringe; and
a flange extending outwardly from the conduit and comprising a first side and a second side, the first side facing towards the oral delivery applicator and the second side facing towards the coupling, wherein at least a portion of the first side of the flange comprises a concavely radiused surface profile defined along a transition between the generally elongate oral delivery applicator and the flange and a convexly radiused surface profile defined along at least a portion of the flange between its engagement with the conduit and an outer periphery thereof, and wherein at least a portion of the second side of the flange comprises a concavely radiused surface profile defined along at least a portion of the flange between its engagement with the conduit and an outer periphery thereof.

28. The oral administration coupler of claim 27, wherein the elongate applicator of the first end is substantially rigid and comprises an oval cross section.

29. The oral administration coupler of claim 27, wherein the coupling comprises outer circumferential collar comprising threads defined on an internal portion thereof, and a transfer port generally axially extending relative to the collar and comprising the conduit extending therethrough.

30. The oral administration coupler of claim 27, wherein the flange is generally circular in shape, and wherein a smooth radiused transition is provided from the generally elongate oral delivery applicator to an outer peripheral portion of the flange so as to provide a continuous and smooth transitional surface therebetween.

31. The oral administration coupler of claim 30, wherein the outer peripheral portion of the flange defines a diameter of between about 20-40 millimeters.

32. The oral administration coupler of claim 31, wherein the outer peripheral portion of the flange defines a diameter of about 32.835 millimeters.

33. The oral administration coupler of claim 27, wherein the conduit extends a distance between the first and second ends of between about 15-35 millimeters.

34. The oral administration coupler of claim 33, wherein the extension of the conduit between the first and second ends defines a distance of about 20.35 millimeters.

35. The oral administration coupler of claim 27, wherein a volume defined within the female connector and within the conduit of the coupler is generally between about 10 mm$^3$ to about 40 mm$^3$.

36. The oral administration coupler of claim 35, wherein the volume defined within the female connector and within the conduit of the coupler is about 20 mm$^3$.

37. The oral administration coupler of claim 27, wherein the flange is substantially large such that choking risks are mitigated.

38. The oral administration coupler of claim 27, wherein the elongate applicator of the first end comprises a circular cross section defining a width of between about 4.5-6 millimeters.

\* \* \* \* \*